US010776645B2

(12) United States Patent
Baek et al.

(10) Patent No.: US 10,776,645 B2
(45) Date of Patent: Sep. 15, 2020

(54) BIOMETRIC SENSOR AND ELECTRONIC DEVICE COMPRISING THE SAME

(71) Applicants:Samsung Electronics Co., Ltd., Gyeonggi-do (KR); Korea Advanced Institute of Science and Technology, Daejeon (KR)

(72) Inventors: Hyun Jae Baek, Seoul (KR); Ki Hun Jeong, Daejeon (KR); Young Jae Oh, Gyeonggi-do (KR); Jung Woo Park, Daejeon (KR); Kyung Won Jang, Daejeon (KR); Chan Sol Hwang, Daejeon (KR); Jae Wook Shin, Gyeonggi-do (KR); Jae Geol Cho, Gyeonggi-do (KR)

(73) Assignee: KOREA ADVANCED INSTITUTE OF SCIENCE AND TECHNOLOGY, Yuseong-Gu, Daejeon (KR)

( * ) Notice: Subject to any disclaimer, the term of this patent is extended or adjusted under 35 U.S.C. 154(b) by 170 days.

(21) Appl. No.: 15/626,367

(22) Filed: Jun. 19, 2017

(65) Prior Publication Data

US 2017/0372152 A1   Dec. 28, 2017

(30) Foreign Application Priority Data

Jun. 27, 2016   (KR) .......................... 10-2016-0080448

(51) Int. Cl.
*G06K 9/00* (2006.01)
*A61B 5/0452* (2006.01)
(Continued)

(52) U.S. Cl.
CPC ........ *G06K 9/00885* (2013.01); *A61B 5/0452* (2013.01); *G06K 9/0012* (2013.01);
(Continued)

(58) Field of Classification Search
CPC .......... G06K 9/00046; G06K 9/00885; G06K 9/0012; G06K 9/2036; G06K 9/00932;
(Continued)

(56) References Cited

U.S. PATENT DOCUMENTS

| 3,407,715 A | 10/1968 | McCutchen |
| 8,391,569 B2 | 3/2013 | Wu |

(Continued)

FOREIGN PATENT DOCUMENTS

| JP | 2004349221 A | * | 12/2004 |
| KR | 10-2004-0039855 A | | 5/2004 |

(Continued)

OTHER PUBLICATIONS

European Search Report dated Aug. 17, 2017.
International Search Report dated Sep. 20, 2017.
European Search Report dated Jun. 18, 2019.

*Primary Examiner* — Kim Y Vu
*Assistant Examiner* — Michael J Vanchy, Jr.
(74) *Attorney, Agent, or Firm* — Cha & Reiter, LLC.

(57) ABSTRACT

A sensor for sensing biometric information includes a light emitting unit that emits a first light ray, a light receiving unit that receives a second light ray, where the second light ray includes a portion of the first light ray reflected by a body of a user, and an optical layer placed over the light emitting unit and the light receiving unit. The optical layer has a first surface facing the light emitting unit and the light receiving unit and a second surface opposite the first surface. The optical layer further includes an asymmetrical protrusion structure formed on the first surface or the second surface and including a plurality of asymmetrical protrusion units. The optical layer may further include a symmetrical protrusion structure formed on the first surface or the second
(Continued)

surface opposite the asymmetrical protrusion structure and including a plurality of symmetrical protrusion units.

18 Claims, 12 Drawing Sheets

(51) Int. Cl.
*G06K 9/20* (2006.01)
*G06K 9/22* (2006.01)

(52) U.S. Cl.
CPC ....... *G06K 9/00046* (2013.01); *G06K 9/2036* (2013.01); *G06K 9/22* (2013.01); *G06K 9/228* (2013.01); *G06K 2009/00932* (2013.01)

(58) Field of Classification Search
CPC .. G06K 9/22; G06K 9/228; A61B 2562/0238; A61B 5/0452; G02B 27/4205; G02B 27/4272; H04N 5/2254
See application file for complete search history.

(56) References Cited

U.S. PATENT DOCUMENTS

| | | | |
|---|---|---|---|
| 8,920,332 B2 | 12/2014 | Hong et al. | |
| 8,948,832 B2 | 2/2015 | Hong et al. | |
| 8,956,303 B2 | 2/2015 | Hong et al. | |
| 9,113,794 B2 | 8/2015 | Hong et al. | |
| 9,113,795 B2 | 8/2015 | Hong et al. | |
| 9,237,855 B2 | 1/2016 | Hong et al. | |
| 9,307,917 B2 | 4/2016 | Hong et al. | |
| 2007/0109438 A1 | 5/2007 | Duparre et al. | |
| 2008/0123908 A1* | 5/2008 | Waldman | G06K 9/00046 382/124 |
| 2009/0316274 A1* | 12/2009 | Lee | G02B 5/045 359/634 |
| 2010/0208952 A1 | 8/2010 | Wu | |
| 2011/0308585 A1 | 12/2011 | Joshi et al. | |
| 2013/0120760 A1 | 5/2013 | Raguin et al. | |
| 2014/0275852 A1* | 9/2014 | Hong | A61B 5/02427 600/301 |
| 2014/0288390 A1 | 9/2014 | Hong et al. | |
| 2014/0288391 A1 | 9/2014 | Hong et al. | |
| 2014/0288392 A1 | 9/2014 | Hong et al. | |
| 2015/0025393 A1 | 1/2015 | Hong et al. | |
| 2015/0025394 A1 | 1/2015 | Hong et al. | |
| 2015/0177884 A1* | 6/2015 | Han | G06F 3/044 345/174 |
| 2015/0201853 A1 | 7/2015 | Hong et al. | |
| 2015/0201854 A1 | 7/2015 | Hong et al. | |
| 2017/0059879 A1* | 3/2017 | Vallius | G02B 27/4205 |
| 2017/0118551 A1 | 4/2017 | Wagner et al. | |
| 2017/0209095 A1 | 7/2017 | Wagner et al. | |
| 2017/0311856 A1* | 11/2017 | Lasarov | A61B 5/02427 |

FOREIGN PATENT DOCUMENTS

| | | |
|---|---|---|
| WO | 2011/110821 A1 | 9/2011 |
| WO | 2013/176573 A1 | 11/2013 |
| WO | 2016/022295 A1 | 2/2016 |
| WO | 2016/066888 A1 | 5/2016 |

\* cited by examiner

BIOMETRIC SENSOR AND ELECTRONIC DEVICE COMPRISING THE SAME

CLAIM OF PRIORITY

This application claims the benefit under 35 U.S.C. § 119(a) of a Korean patent application filed on Jun. 27, 2016 in the Korean Intellectual Property Office and assigned Serial number 10-2016-0080448, the entire disclosure of which is hereby incorporated by reference.

TECHNICAL FIELD

The present disclosure relates to a biometric sensor for sensing biometric signal of a user and an electronic device including the biometric sensor.

BACKGROUND

Electronic devices that serve a variety of functions, such as smartphone, tablet PCs, etc. have proliferated.

In recent years, electronic devices have been developed to provide functions of user authentication by using the biometric information of the user. For example, fingerprint, iris scan, etc. have been used. In other use cases, biometric information, for example, heartrate, is detected and recorded to manage the user's health.

There are various ways in which a biometric sensor may sense biometric information. For example, the biometric information of the user may be detected by shining light, such as infrared and visible light, onto the body of the user and detecting the light reflected by the body.

However, when biometric information is sensed by using light rays, portions of the emitted light rays may be refracted so that they are not incident on the body of the user. Similarly, portions of the reflected light rays may not be incident on the biometric sensor. In these cases, efficiency of the biometric sensor is reduced. Also, in these cases, noises in the biometric signal may increase.

SUMMARY

Aspects of the present disclosure are to address at least the above-mentioned problems and/or disadvantages and to provide at least the advantages described below. Accordingly, an aspect of the present disclosure is to provide a biometric sensor that increases detection efficiency and decreases noises included in a biometric signal.

In accordance with an aspect of the present disclosure, a sensor for sensing biometric information includes a light emitting unit that emits a first light ray, a light receiving unit that receives a second light ray, where the second light ray includes a portion of the first light ray reflected by a body of a user, and an optical layer placed over the light emitting unit and the light receiving unit. The optical layer has a first surface facing the light emitting unit and the light receiving unit and a second surface opposite to the first surface. The optical layer further includes an asymmetrical protrusion structure formed on the first surface or the second surface and including a plurality of asymmetrical protrusion units. The optical layer also may include a symmetrical protrusion structure formed on the first surface or the second surface opposite the asymmetrical protrusion structure and including a plurality of symmetrical protrusion units.

In accordance with an aspect of the present disclosure, an electronic device includes a light emitting unit that emits a first light ray, a light receiving unit that receives a second light ray, where the second light ray includes a portion of the first light ray reflected by a body of a user, a housing including an optical layer, and a processor that determines biometric information of the user based on the second light ray. The optical layer has a first surface facing the light emitting unit and the light receiving unit and a second surface opposite to the first surface. The optical layer further includes an asymmetrical protrusion structure formed on the first surface or the second surface and including a plurality of asymmetrical protrusion units. The optical layer also may include a symmetrical protrusion structure formed on the first surface or the second surface opposite the asymmetrical protrusion structure and including a plurality of symmetrical protrusion units.

In accordance with an aspect of the present disclosure, an electronic device includes a light emitting unit that emits a first light ray, a light receiving unit that receives a second light ray, where the second light ray includes a portion of the first light ray reflected by a body of a user, a housing including an optical layer, and a processor that determines biometric information of the user based on the second light ray. The optical layer includes at least one protrusion structure formed on at least one surface thereof.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
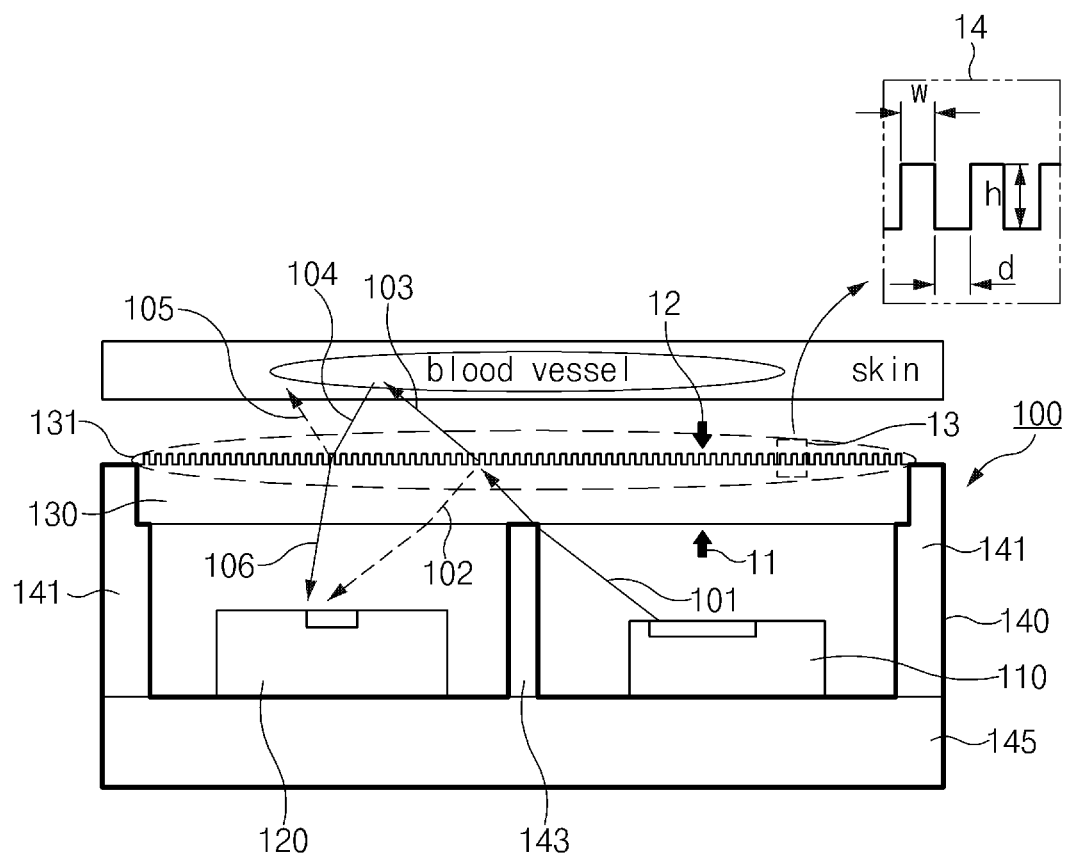
FIG. 1 is a view illustrating a structure of a biometric sensor, according to one embodiment of the present disclosure.

Hereinafter, various embodiments of the present disclosure are disclosed with reference to the accompanying drawings. However, the present disclosure is not intended to be limited by the various embodiments of the present disclosure to a specific embodiment and it is intended that the present disclosure covers all modifications, equivalents, and/or alternatives of the present disclosure provided they come within the scope of the appended claims and their equivalents. With respect to the descriptions of the accompanying drawings, like reference numerals refer to like elements.

The term "include," "comprise," and "have," or "may include," or "may comprise" and "may have" used herein indicates disclosed functions, operations, or existence of elements but does not exclude other functions, operations or elements.

In the disclosure disclosed herein, the expressions "A or B," "at least one of A or/and B," or "one or more of A or/and B," and the like used herein may include any and all combinations of one or more of the associated listed items. For example, the term "A or B," "at least one of A and B," or "at least one of A or B" may refer to all of the case (1) where at least one A is included, the case (2) where at least one B is included, or the case (3) where both of at least one A and at least one B are included.

The terms, such as "first," "second," and the like used herein may refer to various elements of various embodiments of the present disclosure, but do not limit the elements. For example, "a first user device" and "a second user device" may indicate different user devices regardless of the order or priority thereof. For example, without departing the scope of the present disclosure, a first element may be referred to as a second element, and similarly, a second element may be referred to as a first element.

It will be understood that when an element (e.g., a first element) is referred to as being "(operatively or communicatively) coupled with/to" or "connected to" another element (e.g., a second element), it may be directly coupled with/to or connected to the other element or an intervening element (e.g., a third element) may be present. In contrast, when an element (e.g., a first element) is referred to as being "directly coupled with/to" or "directly connected to" another element (e.g., a second element), it should be understood that there are no intervening element (e.g., a third element).

According to the situation, the expression "configured to" used herein may be used as, for example, the expression "suitable for," "having the capacity to," "designed to," "adapted to," "made to," or "capable of" The term "configured to" must not mean only "specifically designed to" in hardware. Instead, the expression "a device configured to" may mean that the device is "capable of" operating together with another device or other components. For example, a "processor configured to (or set to) perform A, B, and C" may mean a dedicated processor (e.g., an embedded processor) for performing a corresponding operation or a generic-purpose processor (e.g., a central processing unit (CPU) or an application processor) which performs corresponding operations by executing one or more software programs which are stored in a memory device.

Terms used in the present disclosure are used to describe specified embodiments and are not intended to limit the scope of the present disclosure. The terms of a singular form may include plural forms unless otherwise specified. All the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal detect unless expressly so defined herein in various embodiments of the present disclosure. In some cases, even if terms are terms which are defined in the specification, they may not be interpreted to exclude embodiments of the present disclosure.

For example, an electronic device according to various embodiments of the present disclosure may include at least one of smartphones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, mobile medical devices, cameras, or wearable devices. According to various embodiments, a wearable device may include at least one of an accessory type of a device (e.g., a timepiece, a ring, a bracelet, an anklet, a necklace, glasses, a contact lens, or a head-mounted-device (HMD)), one-piece fabric or clothes type of a device (e.g., electronic clothes), a body-attached type of a device (e.g., a skin pad or a tattoo), or a bio-implantable type of a device (e.g., implantable circuit).

In some various embodiments of the present disclosure, an electronic device may be a home appliance. The smart home appliance may include at least one of, for example, a television (TV), a digital versatile disc (DVD) player, an audio, a refrigerator, an air conditioner, a cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ or PlayStation™), an electronic dictionary, an electronic key, a camcorder, or an electronic picture frame.

In various embodiments, the electronic devices may include at least one of various medical devices (e.g., various portable medical measurement devices (e.g., blood glucose meters, heart rate meters, blood pressure meters, or thermometers, and the like), a magnetic resonance angiography (MRA), a magnetic resonance imaging (MRI), a computed tomography (CT), scanners, or ultrasonic devices, and the like), navigation devices, global navigation satellite system (GNSS), event data recorders (EDRs), flight data recorders (FDRs), vehicle infotainment devices, electronic equipment for vessels (e.g., navigation systems, gyrocompasses, and the like), avionics, security devices, head units for vehicles, industrial or home robots, automatic teller's machines (ATMs), points of sales (POSs), or internet of things (e.g., light bulbs, various sensors, electric or gas meters, sprinkler devices, fire alarms, thermostats, street lamps, toasters, exercise equipment, hot water tanks, heaters, boilers, and the like).

According to various embodiments, the electronic devices may include at least one of parts of furniture or buildings/structures, electronic boards, electronic signature receiving devices, projectors, or various measuring instruments (e.g., water meters, electricity meters, gas meters, or wave meters, and the like). The electronic devices according to various embodiments of the present disclosure may be one or more combinations of the above-mentioned devices. The electronic devices according to various embodiments of the present disclosure may be flexible electronic devices. Also, electronic devices according to various embodiments of the present disclosure are not limited to the above-mentioned devices, and may include new electronic devices according to technology development Hereinafter, an electronic device according to various embodiments of the present disclosure will be described in more detail with reference to the accompanying drawings. The term "user" used herein may refer to a person who uses an electronic device or may refer to a device (e.g., an artificial intelligence electronic device) that uses an electronic device.

FIG. 1 is a view illustrating a structure of a biometric sensor, according to one embodiment of the present disclosure.

Referring to FIG. 1, a biometric sensor 100 may include a light emitting unit 110 (e.g. a light emitter), a light receiving unit 120 (e.g. a light receiver or detector), an optical layer 130, and a base 140. According to an embodiment, the biometric sensor 100 may sense/detect biometric information (e.g., heartrate, fingerprint, etc.) of a user by using light. According to another embodiment, the biometric sensor 100 may sense the biometric information of the user by using other types of signals such as an ultrasonic signal.

According to an embodiment, the light emitting unit 110 (or a transmission unit if the biometric sensor 100 is using another type of signal) may emit the light rays required to sense the biometric signal. According to an embodiment, the light emitting unit 110 may include an infrared emitting diode that emits infrared rays or a light emitting diode that emits visible light. The light emitted by the light emitting unit 110 may be partially reflected by the body of the user (e.g., skin or blood vessel) and partially absorbed by the body.

According to an embodiment, the light receiving unit 120 (or a reception unit, if the biometric sensor 100 is using another type of signal) may receive light rays reflected by a body of the user. The reflected light rays include a portion of the light rays emitted from the light emitting unit 110, which is the portion reflected by the body of the user. The light reflected by the body of the user may include the biometric information (e.g., heartrate, fingerprint, etc.). According to an embodiment, the light receiving unit 120 may selectively receive light corresponding to a frequency (or a wavelength) of light emitted by the light emitting unit 110. According to an embodiment, the light receiving unit 120 may include a photodiode that detects the light reflected by the body and converts the received light rays into an electrical signal. According to an embodiment, the electrical signal including the biometric information may be transmitted to a sensor integrated circuit (IC) (not illustrated) or a processor (not illustrated) of the electronic device that includes the biometric sensor 100 so that the sensor IC or the processor may determine the biometric information from the electrical signal.

According to an embodiment, the optical layer 130 may be placed over the light emitting unit 110 and the light receiving unit 120. For example, the optical layer 130 may be placed between the light emitting unit 110/the light receiving unit 120 and the body of the user, as shown in FIG. 1, such that light rays emitted by the light emitting unit 110 and light rays received by the light receiving unit 120 pass through the optical layer 130. For example, the light emitted by the light emitting unit 110 may be incident on the body of the user after passing through the optical layer 130, and the light reflected by the body of the user may be received by the light receiving unit 120 after passing through the optical layer 130. The optical layer 130 may be made of a material with high optical transmittance, such as glass or a transparent polymer.

According to an embodiment, the optical layer 130 may include a symmetrical protrusion structure 131 that is formed on at least one surface of the optical layer 130. For example, the optical layer 130 may include the symmetrical protrusion structure 131 formed on a first surface 11 facing the light emitting unit 110 and the light receiving unit 120. Alternatively, the optical layer 130 may include the symmetrical protrusion structure 131 formed on a second surface 12 opposite to the first surface 11. In the embodiment of FIG. 1, the symmetrical protrusion structure 131 is formed on the second surface 12. According to an embodiment, the symmetrical protrusion structure 131 may be formed on a partial region of the first surface 11 and/or the second surface 12. For example, referring to FIG. 1, the symmetrical protrusion structure 131 may be formed on the entire region of the second surface 12, as shown. However, in another example, the symmetrical protrusion structure 131 may be formed in a partial region of the second surface 12 or a partial region of the first surface 11. As another example, the symmetrical protrusion structure 131 may be formed in the entire region of the second surface 12 and a partial region of the first surface 11.

According to an embodiment, the symmetrical protrusion structure 131 may include a plurality of symmetrical protrusion units. Each of the plurality of symmetrical protrusion units may have a symmetrical structure that is symmetrical about a horizontal axis or about a vertical axis. For example, each of the plurality of symmetrical protrusion units may have a cylindrical, hexahedral or conical shape. According to an embodiment, the height of each of the plurality of symmetrical protrusion units may be smaller than the wavelength of the light rays emitted by the light emitting unit 110 or received by the light receiving unit 120. According to an embodiment, the plurality of symmetrical protrusion units may increase the transmittance of the light incident on the optical layer 130. For example, referring to FIG. 1, when the optical layer 130 does not include the symmetrical protrusion structure 131 as shown, the light emitted by the light emitting unit 110 in the first direction 101 may be reflected by the second surface 12 in the second direction 102. This may be disadvantageous because the light reflected in the second direction 102 may not reach the body of the user. However, when the symmetrical protrusion structure 131 is present, the light rays emitted by the light emitting unit 110 in the first direction 101 may be refracted in the third direction 103 after passing through the second surface 12. Thus, the emitted light may be incident on the body of the user and be reflected by the body in the fourth direction 104. The light reflected in the fourth direction 104 may be then incident on the second surface 12. When there is no symmetrical protrusion structure 131, the light incident on the second surface 12 in the fourth direction 104 may be reflected by the second surface 12 in the fifth direction 105. This is also disadvantageous because then the light reflected by the user's body cannot reach the light receiving unit 120. However, when the symmetrical protrusion structure 131 is present, the light incident on the second surface 12 in the fourth direction 104 may be refracted in the sixth direction 106, thereby passing through the second surface 12. The light refracted in the sixth direction 106 then may be incident on the light receiving unit 120. According to the above-described embodiment, when the optical layer 130 includes the symmetrical protrusion structure 131, the light receiving efficiency of the light receiving unit 120 may be improved because the amount of light that is reflected decreases. In addition, because more light is received by the light receiving unit 120, the signal-to-noise ratio of the received light may increase.

Referring to an cutout 14 which is an expanded view of the partial region 13 of the symmetrical protrusion structure 131, the symmetrical protrusion structure 131 may include a plurality of symmetrical protrusion units which have specified height "h" and specified width "w" and are spaced apart from each other by a specified interval (or a distance) "d." According to another embodiment, each of the plurality of symmetrical protrusion units may have different height "h" or different width "w" or may be spaced apart by different distances "d." For each of the plurality of symmetrical protrusion units, its width "w" may vary depending on the height "h".

According to one embodiment, the light transmittance of the optical layer 130 may vary according to the height "h" of each of a plurality of symmetrical protrusion units. For example, when the height "h" of each of the plurality of symmetrical protrusion units is ¼ of the wavelength of light, the light transmittance may be maximized. When the height "h" is greater or smaller than ¼ of the wavelength of the light, light transmittance of the optical layer 130 may decrease. That is, the height "h" of each of the plurality of symmetrical protrusion units may be determined based on the wavelength of the light emitted by the light emitting unit 110.

According to one embodiment, the light transmittance of the optical layer 130 may vary according to the ratio of the area occupied by the plurality of symmetrical protrusion units to the total area occupied by the symmetrical protrusion structure 131. For example, when the ratio of the area occupied by the plurality of symmetrical protrusion units is ½ of the whole area occupied by the symmetrical protrusion structure 131, light transmittance of the optical layer 130 may be maximized. When the ratio is greater than or smaller than ½, light transmittance may decrease.

According to an embodiment, the base 140 may form the housing for the biometric sensor 100. According to an embodiment, the base 140 may include all exterior surfaces of the biometric sensor 100 except for the surface where the optical layer 130 is placed. The light emitting unit 110 and the light receiving unit 120 may be housed within the base 140 and the optical layer 130.

According to an embodiment, the base 140 may include a side wall 141 surrounding the light emitting unit 110 and the light receiving unit 120.

According to an embodiment, the base 140 may include a partition wall 143 that is interposed between the light emitting unit 110 and the light receiving unit 120. The partition wall 143 spatially divides the light emitting unit 110 and the light receiving unit 120. According to an embodiment, the partition wall 143 may optically isolate the light emitting unit 110 and the light receiving unit 120 and reduce the amount of light directly received by the light receiving unit 120 from the light emitting unit 110, thereby reducing noise. According to the embodiment shown FIG. 1, the partition wall 143 contacts the optical layer 130. However, the partition wall 143 may have a specified height and may be configured not to contact the optical layer 130.

According to an embodiment, the base 140 may include a base plate 145 disposed beneath the light emitting unit 110 and the light receiving unit 120. According to an embodiment, at least a part of the base plate 145 may be implemented with a printed circuit board (PCB), and the light emitting unit 110 and the light receiving unit 120 may be electrically connected with the PCB.

Figure 2:
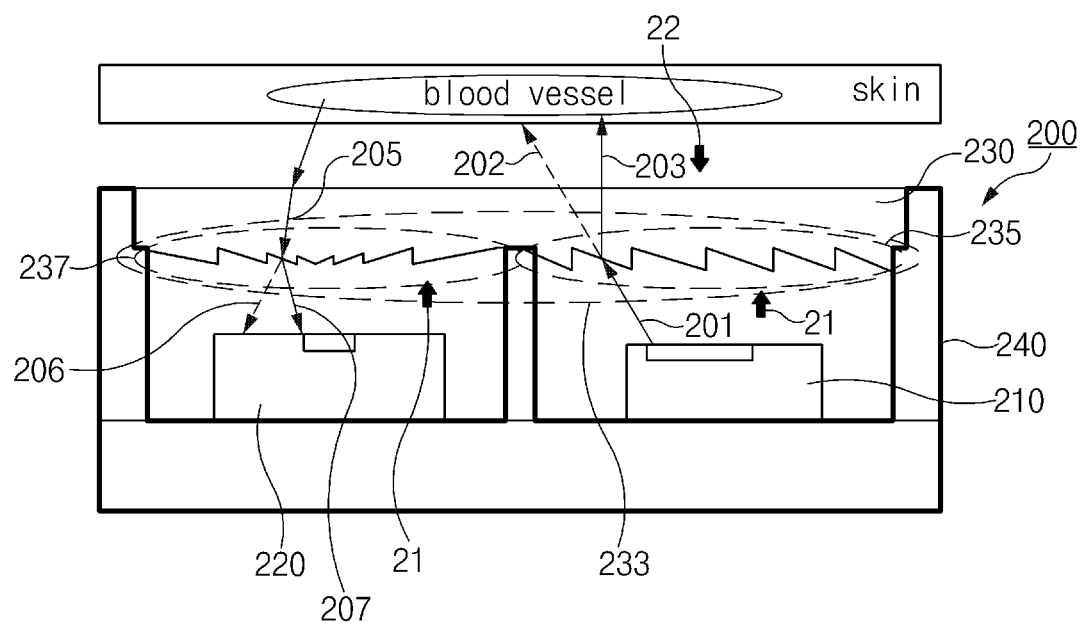
FIG. 2 is a view illustrating a structure of a biometric sensor, according to one embodiment of the present disclosure.

FIG. 2 is a view illustrating a structure of a biometric sensor, according to one embodiment of the present disclosure.

Referring to FIG. 2, a biometric sensor 200 may include a light emitting unit 210, a light receiving unit 220, an optical layer 230, and a base 240. According to an embodiment, the biometric sensor 200 may sense/detect biometric information (e.g., heartrate, fingerprint, etc.) of a user by using light.

The light emitting unit 210, the light receiving unit 220, and the base 240 of the biometric sensor 200 illustrated in FIG. 2 may respectively be the same as or similar to the light emitting unit 110, the light receiving unit 120, and the base 140 illustrated in FIG. 1. In addition, the light emitting unit 210, the light receiving unit 220, and the base 240 of the biometric sensor 200 illustrated in FIG. 2 may respectively execute functions that are the same as or similar to those of the light emitting unit 110, the light receiving unit 120, and the base 140 illustrated in FIG. 1. Therefore, the detailed descriptions thereof may be omitted, and the optical layer 230 will be described.

According to an embodiment, the optical layer 230 may be placed over the light emitting unit 210 and the light receiving unit 220. For example, the optical layer 230 may be placed between the light emitting unit 210/the light receiving unit 220 and the body of the user, as shown in FIG. 2, such that light rays emitted by the light emitting unit 210 and light rays received by the light receiving unit 220 pass through the optical layer 230. For example, the light emitted by the light emitting unit 210 may be reflected by the body of the user after passing through the optical layer 230, and the light reflected by the body of the user may be received by the light receiving unit 220 after passing through the optical layer 230. The optical layer 230 may be made of a material having with high optical transmittance, such as glass or a transparent polymer.

According to an embodiment, the optical layer 230 may include an asymmetrical protrusion structure 233 that is formed on at least one surface of the optical layer 230. For example, the optical layer 230 may include the asymmetrical protrusion structure 233 formed on a first surface 21 facing the light emitting unit 210 and the light receiving unit 220. Alternatively, the optical layer 230 may include the asymmetrical protrusion structure 233 formed on a second surface 22 that is opposite to the first surface 21. In the embodiment of FIG. 2, the asymmetrical protrusion structure 233 is formed on the first surface 21. According to an embodiment, the asymmetrical protrusion structure 233 may be formed in a partial region of the first surface 21 and/or the second surface 22. For example, referring to FIG. 2, the asymmetrical protrusion structure 233 may be formed in the entire region of the first surface 21, as shown. However, in another example, the asymmetrical protrusion structure 233 may be formed in a partial region of the first surface 21 or a partial region of the second surface 22. As another example, the asymmetrical protrusion structure 233 may be formed in the entire region of the second surface 22.

According to an embodiment, the asymmetrical protrusion structure 233 may include a plurality of asymmetrical protrusion units. Each of the plurality of asymmetrical protrusion units may have an asymmetrical structure about a horizontal axis or about a vertical axis. For example, each of the plurality of asymmetrical protrusion units may have a quadrangular pyramid or a conical shape that is inclined in a specified direction. According to an embodiment, the height of each of the plurality of asymmetrical protrusion units may be greater than the wavelength of the light rays emitted by the light emitting unit 210 or received by the light receiving unit 220.

The meaning of "asymmetrical" in the term "asymmetrical protrusion structure" described in the present disclosure means that each of the protrusion units included in the asymmetrical protrusion structure has an asymmetrical shape, and does not mean asymmetry of the asymmetric protrusion structure itself. For example, when the asymmetrical protrusion units included in the asymmetrical protrusion structure 233 are disposed symmetrically with respect to an axis of the asymmetrical protrusion structure 233, the asymmetrical protruding structure 233 itself may have a symmetrical shape.

According to an embodiment, the asymmetrical protrusion structure 233 may include a first asymmetrical protrusion structure 235 and a second asymmetrical protrusion structure 237.

According to an embodiment, the first asymmetrical protrusion structure 235 may be formed in a region corresponding to the light emitting unit 210. According to an embodiment, the first asymmetrical protrusion structure 235 may include a plurality of first asymmetrical protrusion units. The plurality of first asymmetrical protrusion units may have specific shapes such that the light rays incident on the optical layer 230 is refracted away from the light receiving unit 220. For example, referring to FIG. 2, the first asymmetrical protrusion units formed on the first surface 21 of the optical layer 230 may protrude in such a way that is inclined away from the light receiving unit 220. When the optical layer 230 does not include the first asymmetrical protrusion structure 235, the light emitted from the light emitting unit 210 in the first direction 201 may be refracted in the second direction 202 after passing through the first surface 21. But when the first asymmetrical protrusion structure 235 is present on the first surface 21, the light in the first direction 201 may be refracted in the third direction 203, i.e. away from the light receiving unit 220 as compared to the second direction 202, after passing through the first surface 21. Due to the size of the biometric sensor 200 being small, the light emitting unit 210 and the light receiving unit 220 may be close together. In this case, this is advantageous to direct light emitted from the light emitting unit 210 away from the light receiving unit 220 to reduce noise detected by the light receiving unit 220. When the optical layer 230 includes the first asymmetrical protrusion structure 235, the light passing through the optical layer 230 may be refracted away from the light receiving unit 220, as compared to the case without the first asymmetrical protruding structure 235. For this reason, the light receiving efficiency and the signal-to-noise ratio of the light receiving unit 220 may be improved.

According to an embodiment, the second asymmetrical protrusion structure 237 may be formed in a region corresponding to the light receiving unit 220. According to an embodiment, the second asymmetrical protrusion structure 237 may include a plurality of second asymmetrical protrusion units. The plurality of second asymmetrical protrusion units may be shaped such that the light incident on the optical layer 230 is refracted towards an active region of the light receiving unit 220 (i.e. where the photodiode of the light receiving unit 220 is located). In the embodiment shown in FIG. 2, the active region is a center region of the light receiving unit 220. For example, referring to FIG. 2, the second asymmetrical protrusion units may protrude in such a way that is inclined towards the center of the light receiving unit 220. When the optical layer 230 does not include the second asymmetrical protrusion structure 237, light reflected from the body of the user in the fifth direction 205 may be refracted by the first surface 21 in the sixth direction 206. However, when the optical layer 230 includes the second asymmetrical protrusion structure 237, the reflected light may be refracted in the seventh direction 207 (i.e. towards the center of the light receiving unit 220). When the optical layer 230 includes the second asymmetrical protrusion structure 237, the amount of light incident on the active region of the light receiving unit 220 and received by the light receiving unit 220 may increase, and thus the light receiving efficiency of the light receiving unit 220 may be improved.

According to the embodiment shown in FIG. 2, the asymmetrical protrusion structure 233 includes the first asymmetrical protrusion structure 235 and the second asymmetrical protrusion structure 237 on one surface (e.g., a first surface) of the optical layer 230. However, according to other embodiments, the first asymmetrical protrusion structure 235 and the second asymmetrical protrusion structure 237 may be formed on different surfaces of the optical layer 230. Alternatively, the asymmetrical protrusion structure 233 may include only one of the first asymmetrical protrusion structure 235 and the second asymmetrical protrusion structure 237.

According to the embodiment shown in FIG. 2, the optical layer 230 includes only the asymmetrical protrusion structure 233. However, according to other embodiments, the optical layer 230 may further include a symmetrical protrusion structure (e.g., the symmetrical protrusion structure 131 of FIG. 1). For example, the optical layer 230 may further include the symmetrical protrusion structure on the second surface 22.

Figure 3:
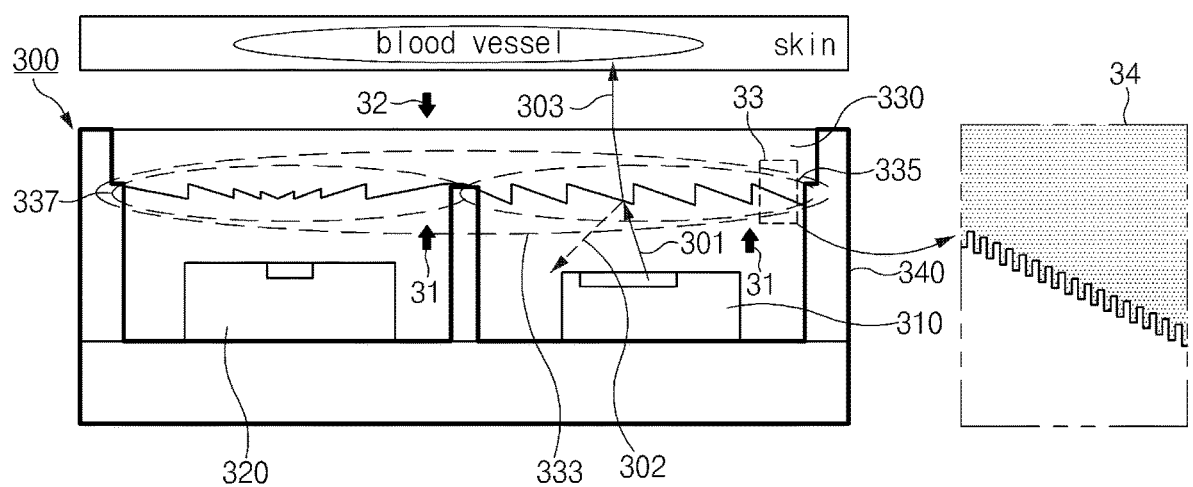
FIG. 3 is a view illustrating a structure of a biometric sensor, according to one embodiment of the present disclosure.

FIG. 3 is a view illustrating a structure of a biometric sensor, according to one embodiment of the present disclosure.

Referring to FIG. 3, a biometric sensor 300 may include a light emitting unit 310, a light receiving unit 320, an optical layer 330, and a base 340. According to an embodiment, the biometric sensor 300 may sense/detect biometric information (e.g., heartrate, fingerprint, etc.) of a user by using light.

The light emitting unit 310, the light receiving unit 320, and the base 340 of the biometric sensor 300 illustrated in FIG. 3 may respectively be the same as or similar to the light emitting unit 110, the light receiving unit 120, and the base 140 illustrated in FIG. 1. In addition, the light emitting unit 310, the light receiving unit 320, and the base 340 of the biometric sensor 300 illustrated in FIG. 3 may respectively execute functions that are the same as or similar to those of the light emitting unit 110, the light receiving unit 120, and the base 140 illustrated in FIG. 1. Therefore, the detailed descriptions thereof may be omitted, and the optical layer 330 will be described.

According to an embodiment, the optical layer 330 may be placed over the light emitting unit 310 and the light receiving unit 320. For example, the optical layer 330 may be placed between the light emitting unit 310/the light receiving unit 320 and the body of the user, as shown in FIG. 3, such that light rays emitted by the light emitting unit 310 and light rays received by the light receiving unit 320 pass through the optical layer 330. For example, the light emitted by the light emitting unit 310 may be reflected by the body of the user after passing through the optical layer 330, and the light reflected by the body of the user may be received by the light receiving unit 320 after passing through the optical layer 330. The optical layer 330 may be made of a material with high optical transmittance, such as glass or a transparent polymer.

According to an embodiment, the optical layer 330 may include an asymmetrical protrusion structure 333 that is formed on at least one surface of the optical layer 330. For example, the optical layer 330 may include the asymmetrical protrusion structure 333 formed on a first surface 31 facing the light emitting unit 310 and the light receiving unit 320. Alternatively, the optical layer 330 may include the asymmetrical protrusion structure 333 formed on a second surface 32 opposite to the first surface 31. In the embodiment of FIG. 3, the asymmetrical protrusion structure 333 is formed on the first surface 31. According to an embodiment, the asymmetrical protrusion structure 333 may be formed in a partial region of the first surface 31 and/or the second surface 32. For example, referring to FIG. 3, the asymmetrical protrusion structure 333 may be formed in the entire region of the first surface 31, as shown. However, in another example, the asymmetrical protrusion structure 333 may be formed in a partial region of the first surface 31 or a partial region of the second surface 32. As another example, the asymmetrical protrusion structure 333 may be formed in the entire region of the second surface 32.

According to an embodiment, the asymmetrical protrusion structure 333 may include a plurality of asymmetrical protrusion units. Each of the plurality of asymmetrical protrusion units may have an asymmetrical structure about a horizontal axis or about a vertical axis. According to an embodiment, the asymmetrical protrusion structure 333 may include a first asymmetrical protrusion structure 335 and a second asymmetrical protrusion structure 337. According to an embodiment, the first asymmetrical protrusion structure 335 may be formed in a region corresponding to the light emitting unit 310. The first asymmetrical protrusion structure 335 may include a plurality of first asymmetrical protrusion units. According to an embodiment, the second asymmetrical protrusion structure 337 may be formed in a region corresponding to the light receiving unit 320. The second asymmetrical protrusion structure 337 may include a plurality of second asymmetrical protrusion units.

According to an embodiment, at least some of the plurality of asymmetrical protrusion units (e.g., the first asymmetrical protrusion units and the second asymmetrical protrusion units) may include a symmetrical protrusion structure or a plurality of symmetrical protrusion units. For example, in at least some of the plurality of asymmetrical protrusion units, a partial region of the asymmetrical protrusion unit may include a symmetrical protrusion structure. Referring to cutout 34, which is an expanded view of the partial region 33 of the first asymmetrical protrusion unit included in the asymmetrical protrusion structure 333, the first asymmetrical protrusion unit may include a symmetrical protrusion structure formed on the surface thereof. According to an embodiment, the symmetrical protrusion structure formed on the surface of the first asymmetrical protrusion unit may increase the transmittance of the light incident on the optical layer 330. For example, referring to FIG. 3, when the first asymmetrical protrusion unit does not include the symmetrical protrusion structure, the light rays emitted by the light emitting unit 310 in the first direction 301 may be reflected by the first surface 31 in the second direction 302. However, when the first asymmetrical protrusion unit includes the symmetrical protrusion structure, the light rays emitted from the light emitting unit 310 may be refracted in the third direction 303 after passing through the first surface 31. The light refracted in the third direction 303 may be incident on the body of the user after passing through the optical layer 330. According to the above-described embodiment, when the asymmetrical protrusion unit includes the symmetrical protrusion structure, the light receiving efficiency of the light receiving unit 320 may be improved because more light is reflected by the body of the user. In addition, because more light is received by the light receiving unit 320, the signal-to-noise ratio of the received light may increase.

Figure 4:
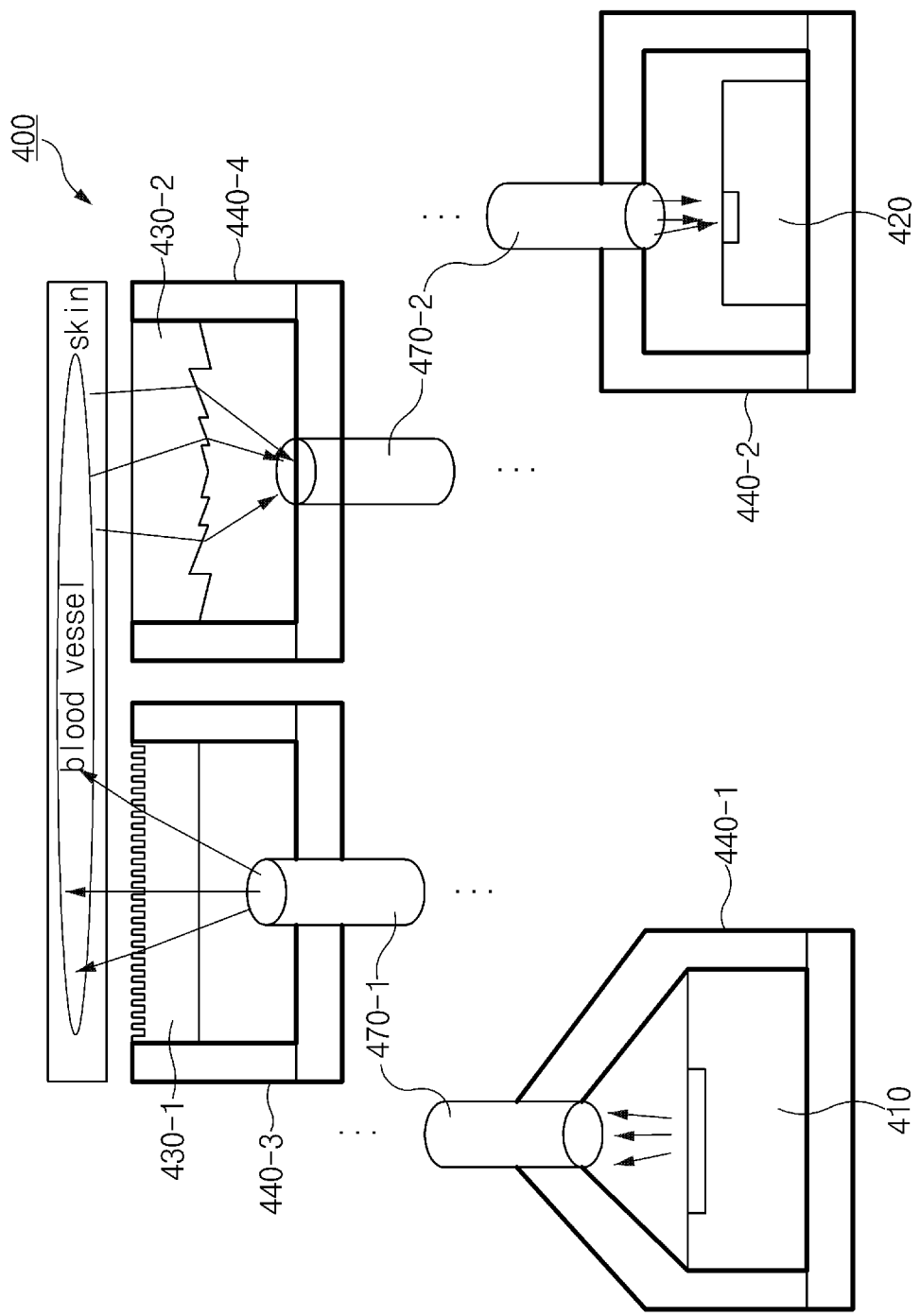
FIG. 4 is a view illustrating a structure of a biometric sensor, according to one embodiment of the present disclosure.

FIG. 4 is a view illustrating a structure of a biometric sensor, according to one embodiment of the present disclosure.

Referring to FIG. 4, a biometric sensor 400 may include a light emitting unit 410, a light receiving unit 420, a plurality of optical layers 430-1 and 430-2, a plurality of bases 440-1, 440-2, 440-3, and 440-4, and a plurality of waveguides 470-1 and 470-2.

The light emitting unit 410 and the light receiving unit 420 of the biometric sensor 400 illustrated in FIG. 4 may respectively be the same as or similar to the light emitting unit 110 and the light receiving unit 120 illustrated in FIG. 1. In addition, the light emitting unit 410 and the light receiving unit 420 of the biometric sensor 400 illustrated in FIG. 4 may respectively execute functions that are the same as or similar to those of the light emitting unit 110 and the light receiving unit 120 illustrated in FIG. 1. Therefore, the detailed descriptions thereof may be omitted, and the plurality of optical layer 430-1 and 430-2, the plurality of bases 440-1, 440-2, 440-3, and 440-4, and the plurality of waveguides 470-1 and 470-2 will be described.

According to an embodiment, the light emitting unit 410 and the light receiving unit 420 may be disposed in different bases. For example, the light emitting unit 410 may be mounted inside the first base 440-1, and the light receiving unit 420 may be mounted inside the second base 440-2. According to an embodiment, the first base 440-1 may be shaped such that the width of the first base 440-1 gradually decreases from the bottom to the top, which may help in guiding the light rays emitted by the light emitting unit 410 into the first waveguide 470-1.

According to an embodiment, the first optical layer 430-1 and the second optical layer 430-2 may be disposed on the upper portions of their respective bases. For example, the first optical layer 430-1 may be disposed on the upper portion of the third base 440-3, and the second optical layer 430-2 may be disposed on the upper portion of the fourth base 440-4.

According to an embodiment, the first optical layer 430-1 may include at least one of a symmetrical protrusion structure (e.g., the symmetrical protrusion structure 131 of FIG. 1) and the first asymmetrical protrusion structure (e.g., the first asymmetrical protrusion structure 235 of FIG. 2) on at least one surface thereof. According to an embodiment, the second optical layer 430-2 may include at least one of the symmetrical protrusion structure and the second asymmetrical protrusion structure (e.g., the second asymmetrical protrusion structure 237 of FIG. 2) on at least one surface thereof. As shown in FIG. 4, the first optical layer 430-1 includes a symmetrical protrusion structure (e.g., the symmetrical protrusion structure 131 of FIG. 1) and the second optical layer 430-2 includes a second asymmetrical protrusion structure (e.g., the second asymmetrical protrusion structure 237 of FIG. 2)

According to an embodiment, each of the plurality of waveguides 470-1 and 470-2 may transmit or guide light. For example, each of the plurality of waveguides 470-1 and 470-2 may employ total internal reflection to transmit light from one end to the other end. For example, each waveguide 470-1 and 470-2 may be an optical fiber.

According to an embodiment, the plurality of waveguides 470-1 and 470-2 may transmit light between the plurality of bases 440-1, 440-2, 440-3, and 440-4. For example, the first waveguide 470-1 may transmit the light from the first base 440-1 including the light emitting unit 410 to the third base 440-3, so that the transmitted light rays are incident on the first optical layer 430-1. The second waveguide 470-2 may transmit the light from the fourth base 440-4 to the second base 440-2 including the light receiving unit 420.

Therefore, in the embodiment shown in FIG. 4, even though the light emitting unit 410 or the light receiving unit 420 are not mounted in the base 430-3 or 430-4 where the optical layers 430-1 and 430-2 are disposed, light rays can still be transmitted/received by the light emitting unit 410 or the light receiving unit 420 to/from the optical layers.

In an embodiment described with reference to FIG. 4, the biometric sensor 400 may include the plurality of waveguides 470-1 and 470-2, but the biometric sensor 400 may include only one of the plurality of waveguides 470-1 and 470-2.

FIG. 5 is a view illustrating a structure of an optical layer, according to one embodiment of the present disclosure.

Referring to FIG. 5, showing various embodiments, at least a partial (e.g., entire or partial) region of the optical layer 530 of the biometric sensor 500 may be curved at a specified curvature. For example, referring to FIG. 5A-5C, the optical layer 530 may have a convex shape when viewed from outside the second surface 52 (i.e., when looking at the second surface 52). As another example, referring to FIG. 5D-5E, the optical layer 530 may have a concave shape when viewed from outside the second surface 52.

Figure 5A:
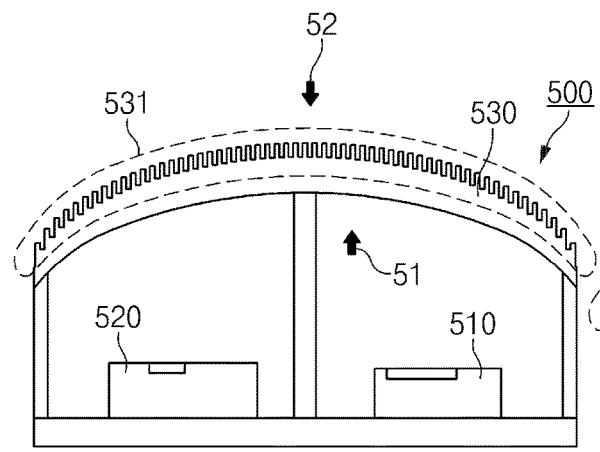
FIG. 5A, FIG. 5B, FIG. 5C, FIG. 5D, FIG. 5E and FIG. 5F are a view illustrating a structure of an optical layer, according to one embodiment of the present disclosure.

Referring to FIG. 5A, the biometric sensor 500 may include the optical layer 530. According to this embodiment, the optical layer 530 may include a symmetrical protrusion structure 531 formed on the second surface 52 opposite the first surface 51 which faces the light emitting unit 510 and the light receiving unit 520. According to this embodiment, the optical layer 530 may have a convex shape when viewed from outside the second surface 52 (i.e., when looking at the second surface 52).

Figure 5B:
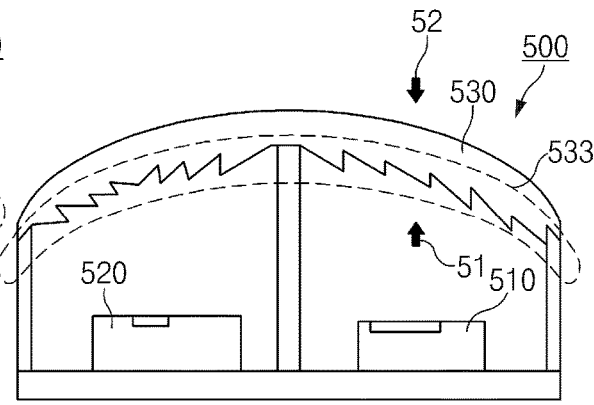

Referring to FIG. 5B, the biometric sensor 500 may include the optical layer 530. According to this embodiment, the optical layer 530 may include the asymmetrical protrusion structure 533 formed on the first surface 51 facing the light emitting unit 510 and the light receiving unit 520. According to this embodiment, the optical layer 530 may have a convex shape when viewed from outside the second surface 52 (i.e., when looking at the second surface 52).

Figure 5C:
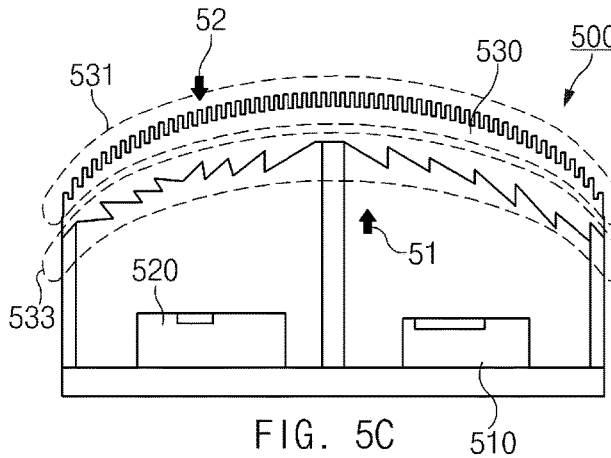

Referring to FIG. 5C, the biometric sensor 500 may include the optical layer 530. According to this embodiment, the optical layer 530 may include the asymmetrical protrusion structure 533 formed on the first surface 51 facing the light emitting unit 510 and the light receiving unit 520 and the symmetrical protrusion structure 531 formed on the second surface 52 opposite to the first surface 51. According to this embodiment, the optical layer 530 may have a convex shape when viewed from outside the second surface 52 (i.e., when looking at the second surface 52).

Figure 5D:
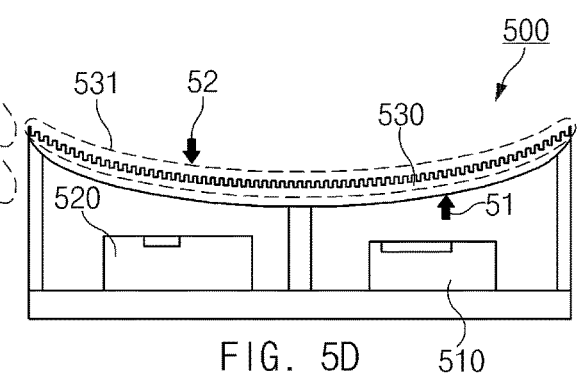

Referring to FIG. 5D, the biometric sensor 500 may include the optical layer 530. According to this embodiment, the optical layer 530 may include the symmetrical protrusion structure 531 formed on the second surface 52 opposite the first surface 51. According to this embodiment, the optical layer 530 may have a concave shape when viewed from outside the second surface 52 (i.e., when looking at the second surface 52).

Figure 5E:
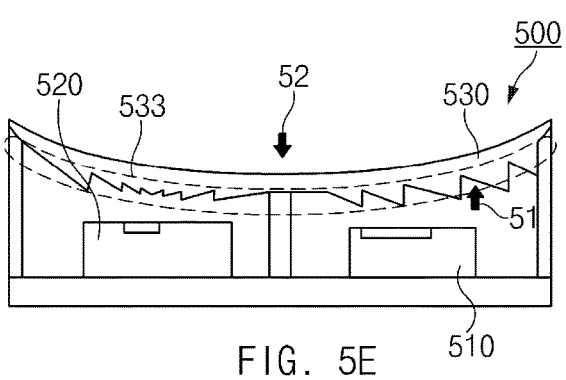

Referring to FIG. 5E, the biometric sensor 500 may include the optical layer 530. According to this embodiment, the optical layer 530 may include the asymmetrical protrusion structure 533 formed on the first surface 51. According to this embodiment, the optical layer 530 may have a concave shape when viewed from outside the second surface 52 (i.e., when looking at the second surface 52).

Figure 5F:
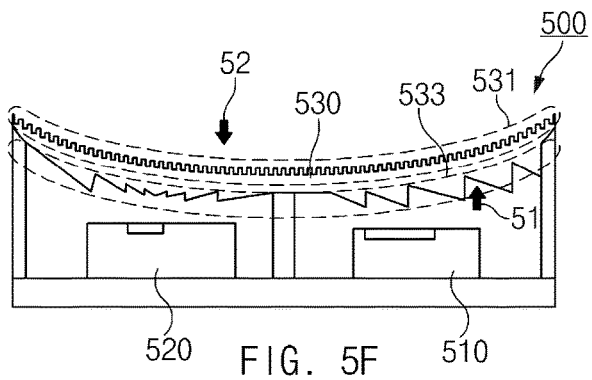

Referring to FIG. 5F, the biometric sensor 500 may include the optical layer 530. According to this embodiment, the optical layer 530 may include the asymmetrical protrusion structure 533 formed on the first surface 51 and the symmetrical protrusion structure 531 formed on the second surface 52 opposite to the first surface 51. According to this embodiment, the optical layer 530 may have a concave shape when viewed from outside the second surface 52 (i.e., when looking at the second surface 52).

Figure 6:
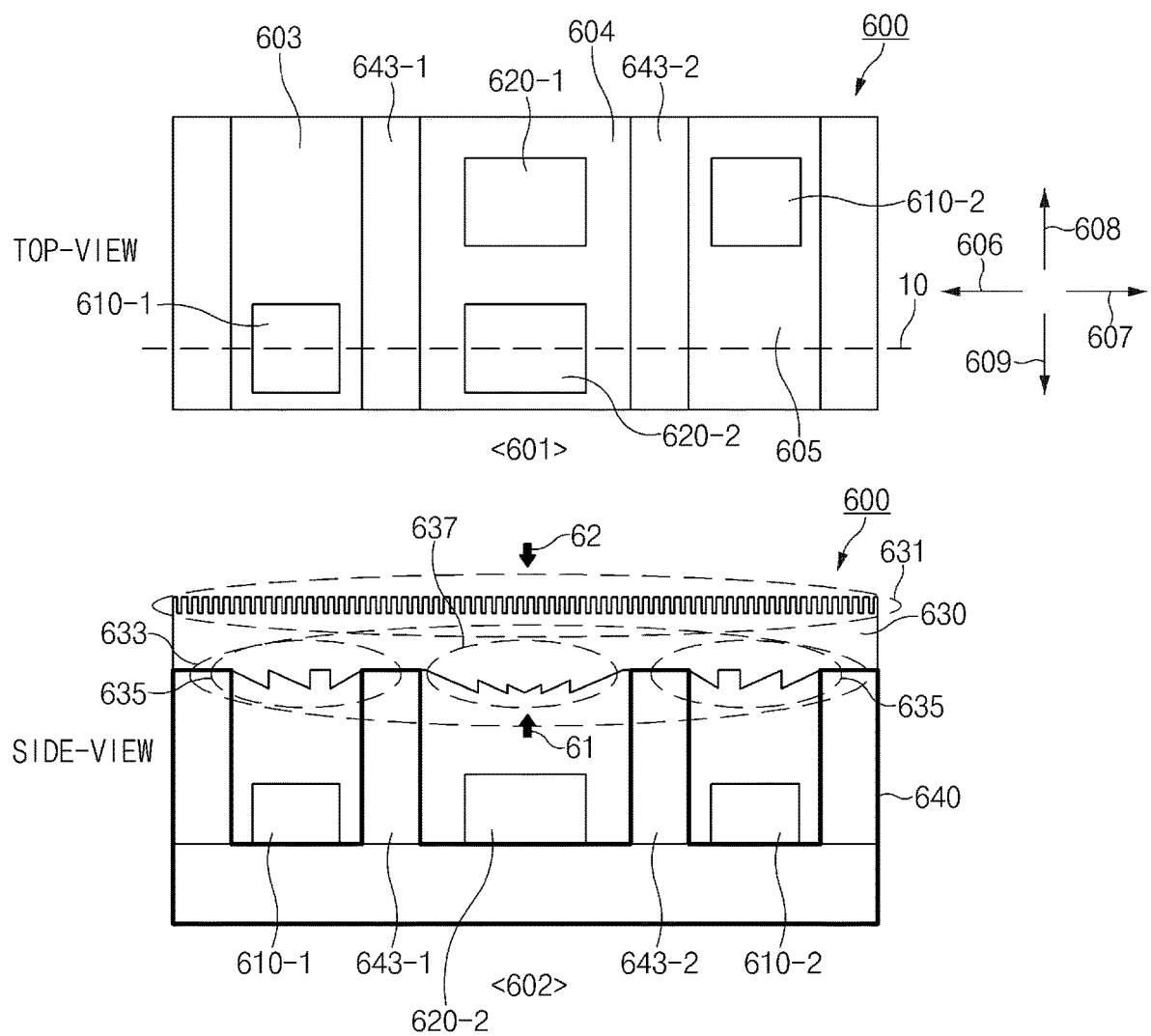
FIG. 6 is a view illustrating a structure of a biometric sensor, according to one embodiment of the present disclosure.

FIG. 6 is a view illustrating a structure of a biometric sensor, according to one embodiment of the present disclosure.

The image 601 illustrated in FIG. 6 illustrates a top-view image of the biometric sensor 600, and the image 602 illustrates a cross-sectional view taken along a line 10 across the biometric sensor 600.

Referring to the image 601 of FIG. 6, the biometric sensor 600 may include a plurality of light emitting units (e.g., a first light emitting unit 610-1 and a second light emitting unit 610-2) and a plurality of light receiving units (e.g., a first light receiving unit 620-1 and a second light receiving unit 620-2).

According to an embodiment, the first light emitting unit 610-1 may operate in conjunction with the first light receiving unit 620-1, and the second light emitting unit 610-2 may operate in conjunction with the second light receiving unit 620-2. For example, the first light emitting unit 610-1 and the first light receiving unit 620-1 may be activated at the same time and deactivated at the same time. In addition, the second light emitting unit 610-2 and the second light receiving unit 620-2 may be activated at the same time and deactivated at the same time.

According to an embodiment, the first light emitting unit 610-1 and the first light receiving unit 620-1 may be activated at times different from when the second light emitting unit 610-2 and the second light receiving unit 620-2 are activated. For example, the second light emitting unit 610-2 and the second light receiving unit 620-2 may be deactivated at the time when the first light emitting unit 610-1 and first light receiving unit 620-1 are activated. Similarly, the first light emitting unit 610-1 and the first light receiving unit 620-1 may be deactivated at the time when the second light emitting unit 610-2 and second light receiving unit 620-2 are activated. Accordingly, using this timing scheme, it is possible to prevent the light emitted from the first light emitting unit 610-1 from being received by the second light receiving unit 620-2 and vice versa.

According to an embodiment, the first light receiving unit 620-1 and the second light receiving unit 620-2 may be disposed in the center region of base 640. In this embodiment, the first light emitting unit 610-1 may be disposed at one side of the center region in the first direction 606, and the second light emitting unit 610-2 may be disposed at the other side in a second direction 607, which is opposite to the first direction 606.

According to an embodiment, the base 640 forming the housing of the biometric sensor 600 may include a plurality of partition walls 643-1 and 643-2 that spatially divide the plurality of light emitting units 610-1 and 610-2 and the plurality of light receiving units 620-1 and 620-2. The internal space of the biometric sensor 600 may be divided into three spaces (e.g., a first space 603, a second space 604, and a third space 605) by the plurality of partition walls 643-1 and 643-2. According to the embodiment shown in FIG. 6, the plurality of partition walls 643-1 and 643-2 contacts the optical layer 630. However, at least some of the plurality of partition walls 643-1 and 643-2 may have a specified height and may be configured not to contact the optical layer 630.

According to an embodiment, the plurality of light receiving units 620-1 and 620-2 may be disposed in the center second space 604. According to an embodiment, the plurality of light receiving unit 620-1 and 620-2 may be disposed in the second space 604 in a direction (e.g., a third direction 608 or a fourth direction 609) perpendicular to the first direction 606 or the second direction 607. For example, the first light receiving unit 620-1 may be disposed in the second space 604 in the third direction 608, and the second light receiving unit 620-2 may be disposed in the fourth direction 609.

According to an embodiment, the first light emitting unit 610-1 may be disposed in the first space 603, and the second light emitting unit 610-2 may be disposed in the third space 605. According to an embodiment, the first light emitting unit 610-1 is located such that the distance between the first light emitting unit 610-1 and the first light receiving unit 620-1 is larger than the distance between the first light emitting unit 610-1 and the second light receiving unit 620-2. Similarly, the second light emitting unit 610-2 is located such that the distance between the second light emitting unit 610-2 and the second light receiving unit 620-2 is larger than the distance between the second light emitting unit 610-2 and the first light receiving unit 620-1. According to the above-described embodiment, the ratio of light that is received by the light receiving units 620-1 and 620-2 after being reflected by the body of the user may increase by maximizing (or adjusting) a distance between the first light emitting unit 610-1 and the first light receiving unit 620-1 or a distance between the second light emitting unit 610-2 and the second light receiving unit 620-2 in a limited space.

According to an embodiment, the light that is received by the plurality of light receiving units 620-1 and 620-2 may be used to generate electrical signals that are in turn transmitted to sensor integrated circuits (IC) (not illustrated) or processors (not illustrated) of the electronic device including the biometric sensor 600. The sensor IC or the processor included in the electronic device may analyze the electrical signal received from the first light receiving unit 620-1 and the second light receiving unit 620-2 and may determine biometric information using the electrical signal. According to the above-described embodiment, noise in the generated electrical signal may be reduced. As such, the biometric information may be accurately sensed.

Referring to 601 of FIG. 6, the biometric sensor 600 may include the optical layer 630 disposed over the plurality of light emitting units 610-1 and 610-2 and the plurality of light receiving units 620-1 and 620-2.

According to an embodiment, the optical layer 630 may include the asymmetrical protrusion structure 633 formed on the first surface 61 facing the plurality of light emitting units 610-1 and 610-2 and the plurality of light receiving units 620-1 and 620-2. The optical layer 630 may also include the symmetrical protrusion structure 631 formed on the second surface 62 opposite to the first surface 61.

According to an embodiment, the asymmetrical protrusion structure 633 may include a first asymmetrical protrusion structure 635 and a second asymmetrical protrusion structure 637. The first asymmetrical protrusion structure 635 may be formed in a region corresponding to each of the plurality of light emitting units 610-1 and 610-2. According to an embodiment, the first asymmetrical protrusion structure 635 may include a plurality of first asymmetrical protrusion units. According to an embodiment, the second asymmetrical protrusion structure 637 may be formed in a region corresponding to the plurality of light receiving units 620-1 and 620-2. The second asymmetrical protrusion structure 637 may include a plurality of second asymmetrical protrusion units. According to an embodiment, the plurality of second asymmetrical protrusion units included in the second asymmetrical protrusion structure 637 may be shaped such that the light incident on the optical layer 630 is refracted to face the active regions in each of the plurality of light receiving units 620-1 and 620-2 (i.e. where the photodiodes of the light receiving units 620-1 and 620-2 are located).

Figure 7:
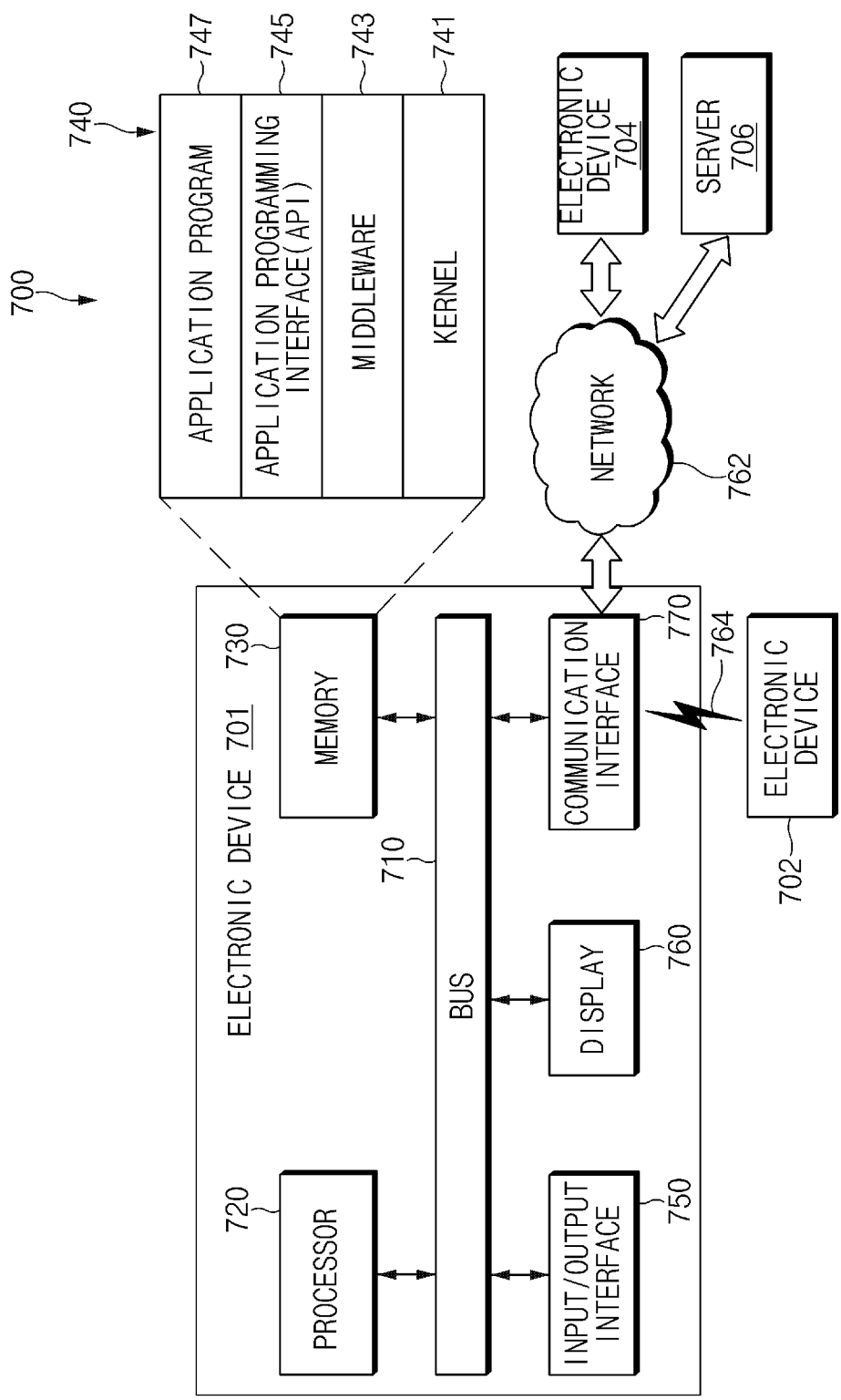
FIG. 7 illustrates an electronic device in a network environment, according to one or more embodiments of the present disclosure.

FIG. 7 illustrates an electronic device in a network environment according to an embodiment of the present disclosure.

An electronic device 701 in a network environment 700 according to one embodiment of the present disclosure will be described with reference to FIG. 7. The electronic device 701 may include a bus 710, a processor 720, a memory 730, an input/output interface 750, a display 760, and a communication interface 770. In various embodiments of the present disclosure, at least one of the foregoing elements may be omitted or another element may be added to the electronic device 701.

The bus 710 may include a circuit for connecting the above-mentioned elements 710 to 770 to each other and transferring communications (e.g., control messages and/or data) among the above-mentioned elements.

The processor 720 may include at least one of a central processing unit (CPU), an application processor (AP), or a communication processor (CP). The processor 720 may perform data processing or an operation related to communication and/or control of at least one of the other elements of the electronic device 701.

The memory 730 may include a volatile memory and/or a nonvolatile memory. The memory 730 may store instructions or data related to at least one of the other elements of the electronic device 701. According to an embodiment of the present disclosure, the memory 730 may store software and/or a program 740. The program 740 may include, for example, a kernel 741, a middleware 743, an application programming interface (API) 745, and/or an application program (or an application) 747. At least a portion of the kernel 741, the middleware 743, or the API 745 may be referred to as an operating system (OS).

The kernel 741 may control or manage system resources (e.g., the bus 710, the processor 720, the memory 730, or the like) used to perform operations or functions of other programs (e.g., the middleware 743, the API 745, or the application program 747). Furthermore, the kernel 741 may provide an interface for allowing the middleware 743, the API 745, or the application program 747 to access individual elements of the electronic device 701 in order to control or manage the system resources.

The middleware 743 may serve as an intermediary so that the API 745 or the application program 747 communicates and exchanges data with the kernel 741.

Furthermore, the middleware 743 may handle one or more task requests received from the application program 747 according to a priority order. For example, the middleware 743 may assign at least one application program 747 a priority for using the system resources (e.g., the bus 710, the processor 720, the memory 730, or the like) of the electronic device 701. For example, the middleware 743 may handle the one or more task requests according to the priority assigned to the at least one application, thereby performing scheduling or load balancing with respect to the one or more task requests.

The API 745, which is an interface for allowing the application 747 to control a function provided by the kernel 741 or the middleware 743, may include, for example, at least one interface or function (e.g., instructions) for file control, window control, image processing, character control, or the like.

The input/output interface 750 may serve to transfer an instruction or data input from a user or another external device to (an)other element(s) of the electronic device 701. Furthermore, the input/output interface 750 may output instructions or data received from (an)other element(s) of the electronic device 701 to the user or another external device.

The display 760 may include, for example, a liquid crystal display (LCD), a light-emitting diode (LED) display, an organic light-emitting diode (OLED) display, a microelectromechanical systems (MEMS) display, or an electronic paper display. The display 760 may present various content (e.g., a text, an image, a video, an icon, a symbol, or the like) to the user. The display 760 may include a touch screen, and may receive a touch, gesture, proximity or hovering input from an electronic pen or a part of a body of the user.

The communication interface 770 may set communications between the electronic device 701 and an external device (e.g., a first external electronic device 702, a second external electronic device 704, or a server 706). For example, the communication interface 770 may be connected to a network 762 via wireless communications or wired communications so as to communicate with the external device (e.g., the second external electronic device 704 or the server 706).

The wireless communications may employ at least one of cellular communication protocols such as long-term evolution (LTE), LTE-advance (LTE-A), code division multiple access (CDMA), wideband CDMA (WCDMA), universal mobile telecommunications system (UMTS), wireless broadband (WiBro), or global system for mobile communications (GSM). The wireless communications may include, for example, a short-range communications 764. The short-range communications may include at least one of wireless fidelity (Wi-Fi), Bluetooth, Bluetooth low energy (BLE), Zigbee, near field communication (NFC), magnetic secure transmission (MST), or GNSS. The GNSS may include, for example, at least one of global positioning system (GPS), global navigation satellite system (GLONASS), BeiDou navigation satellite system (BeiDou), or Galileo, the European global satellite-based navigation system according to a use area or a bandwidth. Hereinafter, the term "GPS" and the term "GNSS" may be interchangeably used.

The wired communications may include at least one of universal serial bus (USB), high definition multimedia interface (HDMI), recommended standard 832 (RS-232), plain old telephone service (POTS), or the like. The network 762 may include at least one of telecommunications networks, for example, a computer network (e.g., local area network (LAN) or wide area network (WAN)), the Internet, or a telephone network.

The types of the first external electronic device 702 and the second external electronic device 704 may be the same as or different from the type of the electronic device 701. According to an embodiment of the present disclosure, the server 706 may include a group of one or more servers. A portion or all of operations performed in the electronic device 701 may be performed in one or more other electronic devices (e.g., the first external electronic device 702, the second external electronic device 704, or the server 706). When the electronic device 701 should perform a certain function or service automatically or in response to a request, the electronic device 701 may request at least a portion of functions related to the function or service from another device (e.g., the first external electronic device 702, the second external electronic device 704, or the server 706) instead of or in addition to performing the function or service for itself. The other electronic device (e.g., the first external electronic device 702, the second external electronic device 704, or the server 706) may perform the requested function or additional function, and may transfer a result of the performance to the electronic device 701. The electronic device 701 may use a received result itself or additionally process the received result to provide the requested function or service. To this end, for example, a cloud computing technology, a distributed computing technology, or a client-server computing technology may be used.

Figure 8:
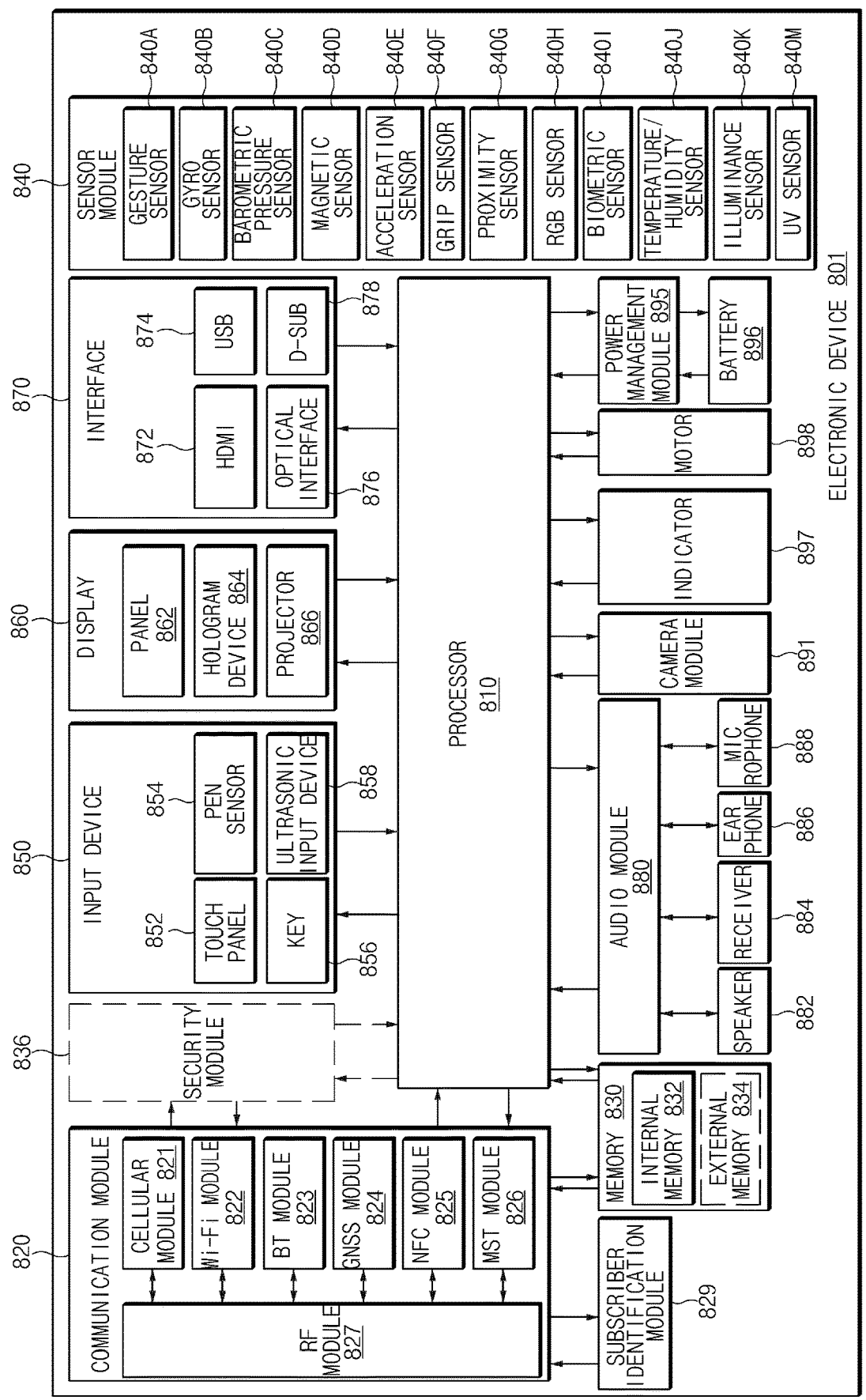
FIG. 8 is a block diagram illustrating an electronic device, according to one or more embodiments of the present disclosure.

FIG. 8 is a block diagram illustrating an electronic device according to an embodiment of the present disclosure.

Referring to FIG. 8, an electronic device 801 may include, for example, a part or the entirety of the electronic device 701 illustrated in FIG. 7. The electronic device 801 may include at least one processor (e.g., AP) 810, a communication module 820, a subscriber identification module (SIM) 829, a memory 830, a sensor module 840, an input device 850, a display 860, an interface 870, an audio module 880, a camera module 891, a power management module 895, a battery 896, an indicator 897, and a motor 898.

The processor 810 may run an operating system or an application program so as to control a plurality of hardware or software elements connected to the processor 810, and may process various data and perform operations. The processor 810 may be implemented with, for example, a system on chip (SoC). According to an embodiment of the present disclosure, the processor 810 may further include a graphic processing unit (GPU) and/or an image signal processor. The processor 810 may include at least a portion (e.g., a cellular module 821) of the elements illustrated in FIG. 8. The processor 810 may load, on a volatile memory, an instruction or data received from at least one of other elements (e.g., a nonvolatile memory) to process the instruction or data, and may store various data in a nonvolatile memory. The processor 810 may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc.

The communication module 820 may have a configuration that is the same as or similar to that of the communication interface 770 of FIG. 7. The communication module 820 may include, for example, a cellular module 821, a Wi-Fi module 822, a Bluetooth module 823, a GNSS module 824 (e.g., a GPS module, a GLONASS module, a BeiDou module, or a Galileo module), an NFC module 825, an MST module 826 and a radio frequency (RF) module 827.

The cellular module 821 may provide, for example, a voice call service, a video call service, a text message service, or an Internet service through a communication network. The cellular module 821 may identify and authenticate the electronic device 801 in the communication network using the subscriber identification module 829 (e.g., a SIM card). The cellular module 821 may perform at least a part of functions that may be provided by the processor 810. The cellular module 821 may include a communication processor (CP).

Each of the Wi-Fi module 822, the Bluetooth module 823, the GNSS module 824, the NFC module 825 and the MST module 826 may include, for example, a processor for processing data transmitted/received through the modules. According to some various embodiments of the present disclosure, at least a part (e.g., two or more) of the cellular module 821, the Wi-Fi module 822, the Bluetooth module 823, the GNSS module 824, the NFC module 825 and the MST module 826 may be included in a single integrated chip (IC) or IC package.

The RF module 827 may transmit/receive, for example, communication signals (e.g., RF signals). The RF module 827 may include, for example, a transceiver, a power amp module (PAM), a frequency filter, a low noise amplifier (LNA), an antenna, or the like. According to another embodiment of the present disclosure, at least one of the cellular module 821, the Wi-Fi module 822, the Bluetooth module 823, the GNSS module 824, the NFC module 825 and the MST module 826 may transmit/receive RF signals through a separate RF module.

The SIM 829 may include, for example, an embedded SIM and/or a card containing the subscriber identity module, and may include unique identification information (e.g., an integrated circuit card identifier (ICCID)) or subscriber information (e.g., international mobile subscriber identity (IMSI)).

The memory 830 (e.g., the memory 730) may include, for example, an internal memory 832 or an external memory 834. The internal memory 832 may include at least one of a volatile memory (e.g., a dynamic RAM (DRAM), a static RAM (SRAM), a synchronous dynamic RAM (SDRAM), or the like), a nonvolatile memory (e.g., a one-time programmable ROM (OTPROM), a programmable ROM (PROM), an erasable and programmable ROM (EPROM), an electrically erasable and programmable ROM (EEPROM), a mask ROM, a flash ROM, a flash memory (e.g., a NAND flash memory, a NOR flash memory, or the like)), a hard drive, or a solid state drive (SSD).

The external memory 834 may include a flash drive such as a compact flash (CF), a secure digital (SD), a Micro-SD, a Mini-SD, an extreme digital (xD), a MultiMediaCard (MMC), a memory stick, or the like. The external memory 834 may be operatively and/or physically connected to the electronic device 801 through various interfaces.

A security module 836, which is a module including a storage space that is higher in security level than the memory 830, may be a circuit for securing safe data storage and protected execution circumstances. The security module 836 may be implemented with an additional circuit and may include an additional processor. The security module 836 may be present in an attachable smart chip or SD card, or may include an embedded secure element (eSE), which is installed in a fixed chip. Additionally, the security module 836 may be driven in another OS which is different from the OS of the electronic device 801. For example, the security module 836 may operate based on a java card open platform (JCOP) OS.

The sensor module 840 may, for example, measure physical quantity or detect an operation state of the electronic device 801 so as to convert measured or detected information into an electrical signal. The sensor module 840 may include, for example, at least one of a gesture sensor 840A, a gyro sensor 840B, a barometric pressure sensor 840C, a magnetic sensor 840D, an acceleration sensor 840E, a grip sensor 840F, a proximity sensor 840G, a color sensor 840H (e.g., a red/green/blue (RGB) sensor), a biometric sensor 840I, a temperature/humidity sensor 840J, an illumination sensor 840K, or an ultraviolet (UV) sensor 840M. Additionally or alternatively, the sensor module 840 may include, for example, an olfactory sensor (E-nose sensor), an electromyography (EMG) sensor, an electroencephalogram (EEG) sensor, an electrocardiogram (ECG) sensor, an infrared (IR) sensor, an iris recognition sensor, and/or a fingerprint sensor. The sensor module 840 may further include a control circuit for controlling at least one sensor included therein. In some various embodiments of the present disclosure, the electronic device 801 may further include a processor configured to control the sensor module 840 as a part of the processor 810 or separately, so that the sensor module 840 is controlled while the processor 810 is in a sleep state.

The input device 850 may include, for example, a touch panel 852, a (digital) pen sensor 854, a key 856, or an ultrasonic input device 858. The touch panel 852 may employ at least one of capacitive, resistive, infrared, and ultraviolet sensing methods. The touch panel 852 may further include a control circuit. The touch panel 852 may further include a tactile layer so as to provide a haptic feedback to a user.

The (digital) pen sensor 854 may include, for example, a sheet for recognition which is a part of a touch panel or is separate. The key 856 may include, for example, a physical button, an optical button, or a keypad. The ultrasonic input device 858 may sense ultrasonic waves generated by an input tool through a microphone 888 so as to identify data corresponding to the ultrasonic waves sensed.

The display 860 (e.g., the display 760) may include a panel 862, a hologram device 864, or a projector 866. The panel 862 may have a configuration that is the same as or similar to that of the display 760 of FIG. 7. The panel 862 may be, for example, flexible, transparent, or wearable. The panel 862 and the touch panel 852 may be integrated into a single module. The hologram device 864 may display a stereoscopic image in a space using a light interference phenomenon. The projector 866 may project light onto a screen so as to display an image. The screen may be disposed in the inside or the outside of the electronic device 801. According to an embodiment of the present disclosure, the display 860 may further include a control circuit for controlling the panel 862, the hologram device 864, or the projector 866.

The interface 870 may include, for example, an HDMI 872, a USB 874, an optical interface 876, or a D-subminiature (D-sub) 878. The interface 870, for example, may be included in the communication interface 770 illustrated in FIG. 7. Additionally or alternatively, the interface 870 may include, for example, a mobile high-definition link (MHL) interface, an SD card/multi-media card (MMC) interface, or an infrared data association (IrDA) interface.

The audio module 880 may convert, for example, a sound into an electrical signal or vice versa. At least a portion of elements of the audio module 880 may be included in the input/output interface 750 illustrated in FIG. 7. The audio module 880 may process sound information input or output through a speaker 882, a receiver 884, an earphone 886, or the microphone 888.

The camera module 891 is, for example, a device for shooting a still image or a video. According to an embodiment of the present disclosure, the camera module 891 may include at least one image sensor (e.g., a front sensor or a rear sensor), a lens, an image signal processor (ISP), or a flash (e.g., an LED or a xenon lamp).

The power management module 895 may manage power of the electronic device 801. According to an embodiment of the present disclosure, the power management module 895 may include a power management integrated circuit (PMIC), a charger integrated circuit (IC), or a battery or gauge. The PMIC may employ a wired and/or wireless charging method. The wireless charging method may include, for example, a magnetic resonance method, a magnetic induction method, an electromagnetic method, or the like. An additional circuit for wireless charging, such as a coil loop, a resonant circuit, a rectifier, or the like, may be further included. The battery gauge may measure, for example, a remaining capacity of the battery 896 and a voltage, current or temperature thereof while the battery is charged. The battery 896 may include, for example, a rechargeable battery and/or a solar battery.

The indicator 897 may display a specific state of the electronic device 801 or a part thereof (e.g., the processor 810), such as a booting state, a message state, a charging state, or the like. The motor 898 may convert an electrical signal into a mechanical vibration, and may generate a vibration or haptic effect. Although not illustrated, a processing device (e.g., a GPU) for supporting a mobile TV may be included in the electronic device 801. The processing device for supporting a mobile TV may process media data according to the standards of digital multimedia broadcasting (DMB), digital video broadcasting (DVB), Media-FLO™, or the like.

Figure 9:
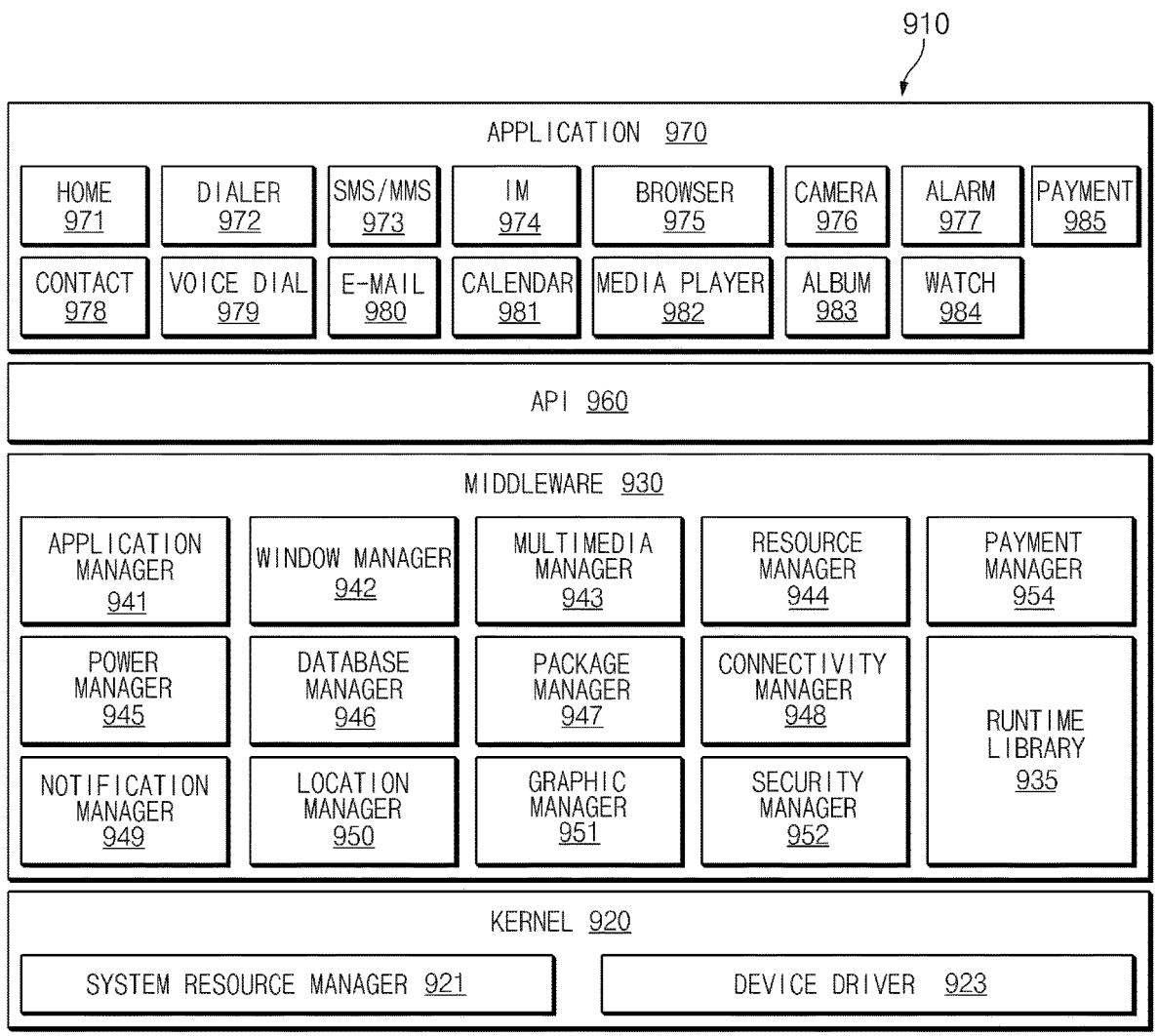
FIG. 9 is a block diagram of a program module, according to one or more embodiments of the present disclosure.

FIG. 9 is a block diagram illustrating a program module according to an embodiment of the present disclosure.

Referring to FIG. 9, a program module 910 (e.g., the program 740) may include an operating system (OS) for controlling a resource related to an electronic device (e.g., the electronic device 701) and/or various applications (e.g., the application program 747) running on the OS. The operating system may be, for example, Android, iOS, Windows, Symbian, Tizen, or the like.

The program module 910 may include a kernel 920, a middleware 930, an API 960, and/or an application 970. At least a part of the program module 910 may be preloaded on an electronic device or may be downloaded from an external electronic device (e.g., the first external electronic device 702, the second external electronic device 704, or the server 706).

The kernel 920 (e.g., the kernel 741) may include, for example, a system resource manager 921 or a device driver 923. The system resource manager 921 may perform control, allocation, or retrieval of a system resource. According to an embodiment of the present disclosure, the system resource manager 921 may include a process management unit, a memory management unit, a file system management unit, or the like. The device driver 923 may include, for example, a display driver, a camera driver, a Bluetooth driver, a shared memory driver, a USB driver, a keypad driver, a Wi-Fi driver, an audio driver, or an inter-process communication (IPC) driver.

The middleware 930, for example, may provide a function that the applications 970 require in common, or may provide various functions to the applications 970 through the API 960 so that the applications 970 may efficiently use limited system resources in the electronic device. According to an embodiment of the present disclosure, the middleware 930 (e.g., the middleware 743) may include at least one of a runtime library 935, an application manager 941, a window manager 942, a multimedia manager 943, a resource manager 944, a power manager 945, a database manager 946, a package manager 947, a connectivity manager 948, a notification manager 949, a location manager 950, a graphic manager 951, a security manager 952 and a payment manager 954.

The runtime library 935 may include, for example, a library module that a complier uses to add a new function through a programming language while the application 970 is running. The runtime library 935 may perform a function for input/output management, memory management, or an arithmetic function.

The application manager 941 may mange, for example, a life cycle of at least one of the applications 970. The window manager 942 may manage a GUI resource used in a screen. The multimedia manager 943 may recognize a format required for playing various media files and may encode or decode a media file using a codec matched to the format. The resource manager 944 may manage a resource such as a source code, a memory, or a storage space of at least one of the applications 970.

The power manager 945, for example, may operate together with a basic input/output system (BIOS) to manage a battery or power and may provide power information required for operating the electronic device. The database manager 946 may generate, search, or modify a database to be used in at least one of the applications 970. The package manager 947 may manage installation or update of an application distributed in a package file format.

The connectivity manager 948 may manage wireless connection of Wi-Fi, Bluetooth, or the like. The notification manager 949 may display or notify an event such as message arrival, appointments, and proximity alerts in such a manner as not to disturb a user. The location manager 950 may manage location information of the electronic device. The graphic manager 951 may manage a graphic effect to be provided to a user or a user interface related thereto. The security manager 952 may provide various security functions required for system security or user authentication. According to an embodiment of the present disclosure, in the case in which an electronic device (e.g., the electronic device 701) includes a phone function, the middleware 930 may further include a telephony manager for managing a voice or video call function of the electronic device.

The middleware 930 may include a middleware module for forming a combination of various functions of the above-mentioned elements. The middleware 930 may provide a module specialized for each type of an operating system to provide differentiated functions. Furthermore, the middleware 930 may delete a part of existing elements or may add new elements dynamically.

The API 960 (e.g., the API 745) which is, for example, a set of API programming functions may be provided in different configurations according to an operating system. For example, in the case of Android or iOS, one API set may be provided for each platform, and, in the case of Tizen, at least two API sets may be provided for each platform.

The application 970 (e.g., the application program 747), for example, may include at least one application capable of performing functions such as a home 971, a dialer 972, an SMS/MMS 973, an instant message (IM) 974, a browser 975, a camera 976, an alarm 977, a contact 978, a voice dial 979, an e-mail 980, a calendar 981, a media player 982, an album 983, a clock 984, a payment 985, health care (e.g., measure an exercise amount or blood sugar), or environmental information provision (e.g., provide air pressure, humidity, or temperature information).

According to an embodiment of the present disclosure, the application 970 may include an information exchange application for supporting information exchange between the electronic device (e.g., the electronic device 701) and an external electronic device (e.g., the first external electronic device 702 or the second external electronic device 704). The information exchange application may include, for example, a notification relay application for relaying specific information to the external electronic device or a device management application for managing the external electronic device.

For example, the notification relay application may have a function for relaying, to an external electronic device (e.g., the first external electronic device 702 or the second external electronic device 704), notification information generated in another application (e.g., an SMS/MMS application, an e-mail application, a health care application, an environmental information application, or the like) of the electronic device. Furthermore, the notification relay application may receive notification information from the external electronic device and may provide the received notification information to the user.

The device management application, for example, may manage (e.g., install, delete, or update) at least one function (e.g., turn-on/turn off of the external electronic device itself (or some elements) or the brightness (or resolution) adjustment of a display) of the external electronic device (e.g., the first external electronic device 702 or the second external electronic device 704) communicating with the electronic device, an application running in the external electronic device, or a service (e.g., a call service, a message service, or the like) provided from the external electronic device.

According to an embodiment of the present disclosure, the application 970 may include a specified application (e.g., a healthcare application of a mobile medical device) according to an attribute of the external electronic device (e.g., the first external electronic device 702 or the second external electronic device 704). The application 970 may include an application received from an external electronic device (e.g., the first external electronic device 702 or the second external electronic device 704). The application 970 may include a preloaded application or a third-party application downloadable from a server. The names of the elements of the program module 910 illustrated may vary with the type of an operating system.

According to one or more embodiments of the present disclosure, at least a part of the program module 910 may be implemented with software, firmware, hardware, or a combination thereof. At least a part of the program module 910, for example, may be implemented (e.g., executed) by a processor (e.g., the processor 810). At least a part of the program module 910 may include, for example, a module, a program, a routine, sets of instructions, or a process for performing at least one function.

Figure 10:
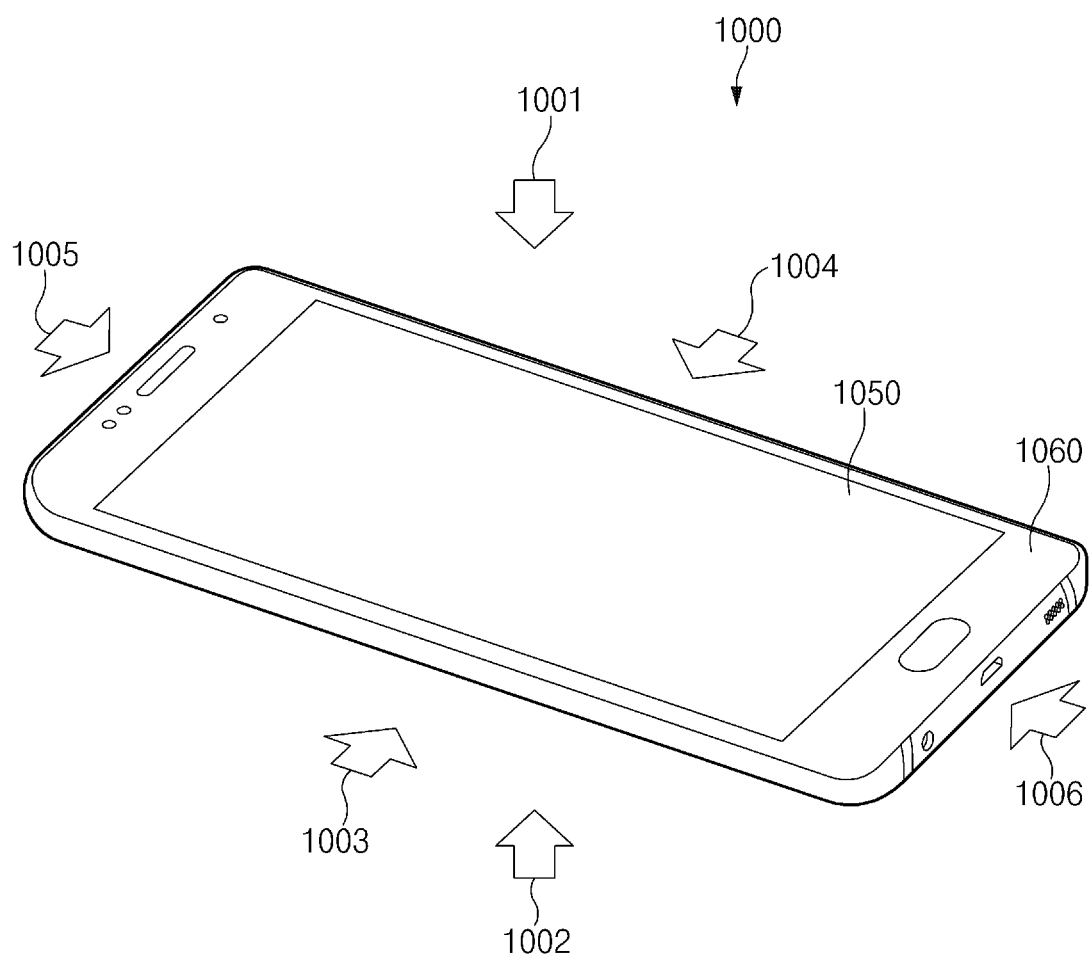
FIG. 10 illustrates an appearance of an electronic device, according to an embodiment of the present disclosure.

FIG. 10 illustrates an appearance of an electronic device, according to an embodiment of the present disclosure.

Referring to FIG. 10, according to an embodiment, an electronic device 1000 may include a display 1050 (e.g. a touch screen) and a housing 1060. Various circuits, modules, or the like such as a processor, a memory, and the like may be disposed inside the housing 1060.

According to one embodiment, the display 1050 may be disposed on a front surface of the electronic device 1000. For example, the display 1050 may be disposed in the housing 1060 facing an upper direction and be exposed through a window in the front surface 1001.

According to one embodiment, the display 1050 may output content (e.g., text, image, video, icon, widget, symbol, etc.) and may receive a touch input (e.g., including touch, hovering input, or "a force touch") from a user. To this end, the display 1050 may include, for example, a display panel, a touch panel, a fingerprint sensor, and/or a pressure sensor. The display panel, the touch panel, the fingerprint sensor, and/or the pressure sensor may be disposed to overlap with each other.

According to one embodiment, the display 1050 may be disposed on the front surface 1001 of the electronic device 1000 and may further extend from the front surface 1001 to at least one side surface. For example, the display 1050 may extend to a left-side surface 1003 and/or a right-side surface 1004. The display 1050 may be exposed through windows in the left-right side surfaces 1003 and 1004 in addition to the front surface 1001 when the window in the front surface 1001 extends to the left-side surface 1003 and/or the right-side surface 1004.

According to one embodiment, the housing 1060 may include the front surface 1001 facing in the upper direction, the rear surface 1002 opposite to the front surface 1001, and side surface between the front surface 1001 and the rear surface 1002. The side surfaces may include the left-side surface 1003 facing in the left-side direction, the right-side surface 1004 facing in the right-side direction, a upper-side surface 1005 facing in an upper-side direction, and a bottom-side surface 1006 facing in a bottom-side direction.

According to one embodiment, to protect various elements in the electronic device 1000 from an external shock or dust, the housing 1060 may be formed with a plastic injection molding material, a conductive material (e.g., metal), or a combination thereof. According to an embodiment, the front surface 1001 of the housing 1060 may correspond to the cover glass of the electronic device 1000, the side surfaces 1003, 1004, 1005, and 1006 of the housing 1060 may correspond to side surface members of the rear case or rear plate of the electronic device 1000, and the rear surface 1002 of the housing 1060 may correspond to the back cover for the battery of the electronic device 1000.

Figure 11:
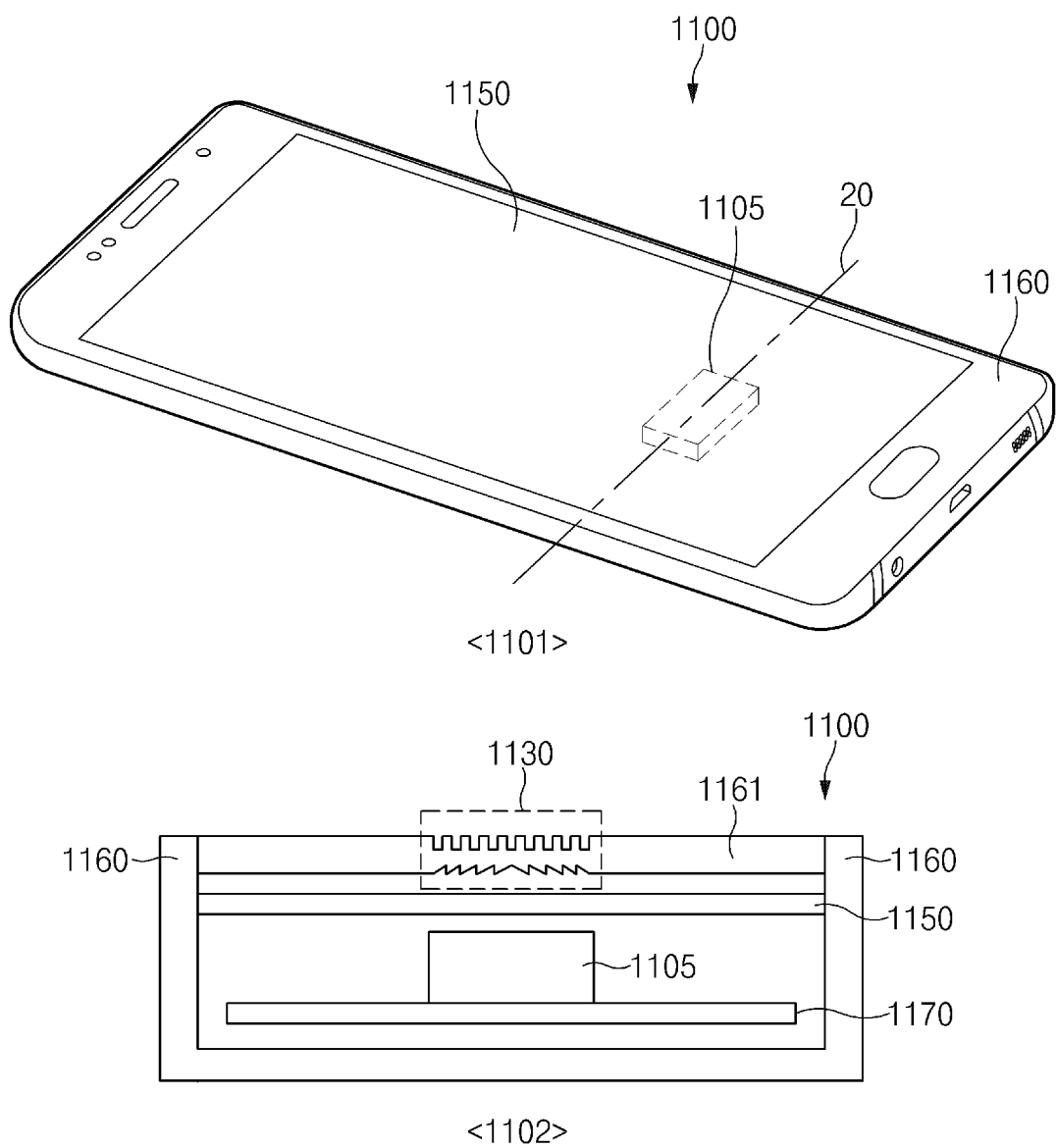
FIG. 11 is a view illustrating a structure of an electronic device, according to one embodiment of the present disclosure.

FIG. 11 is a view illustrating a structure of an electronic device, according to one embodiment of the present disclosure.

The image 1101 illustrates a perspective view of an electronic device 1100, and an image 1102 illustrates a cross-sectional view taken along a line 20 across the electronic device 1100.

Referring to the image 1101 of FIG. 11, the electronic device 1100 may include a biometric sensor 1105, a display 1150, and a housing 1160. According to an embodiment, the biometric sensor 1105 may be disposed inside the housing 1160 and may be disposed in a region overlapping with the display 1150 when viewed from the front surface of the electronic device 1100.

Referring to the image 1102 of FIG. 11, the biometric sensor 1105 may be disposed under the display 1150 in the housing 1160. According to an embodiment, the housing 1160 may include a cover glass 1161 on the front surface (e.g., on the display 1150) of the electronic device 1100. According to an embodiment, the cover glass 1161 may include an optical layer 1130 in at least a partial region of the cover glass 1161. For example, the cover glass 1161 may include the optical layer 1130 in a region corresponding to the biometric sensor 1105. The optical layer 1130 may correspond to the optical layers 130, 230, 330, 430, 530, and 630 according to various embodiments illustrated in FIGS. 1 to 6.

According to an embodiment, the electronic device 1100 may include a printed circuit board (PCB) 1170 (e.g., a flexible printed circuit board (FPCB)) in the housing 1160. The PCB 1170 may be electrically connected with the biometric sensor 1105 and may transmit the electrical signal generated by the biometric sensor 1105 to the sensor IC or the processor included in the electronic device 1100.

Figure 12:
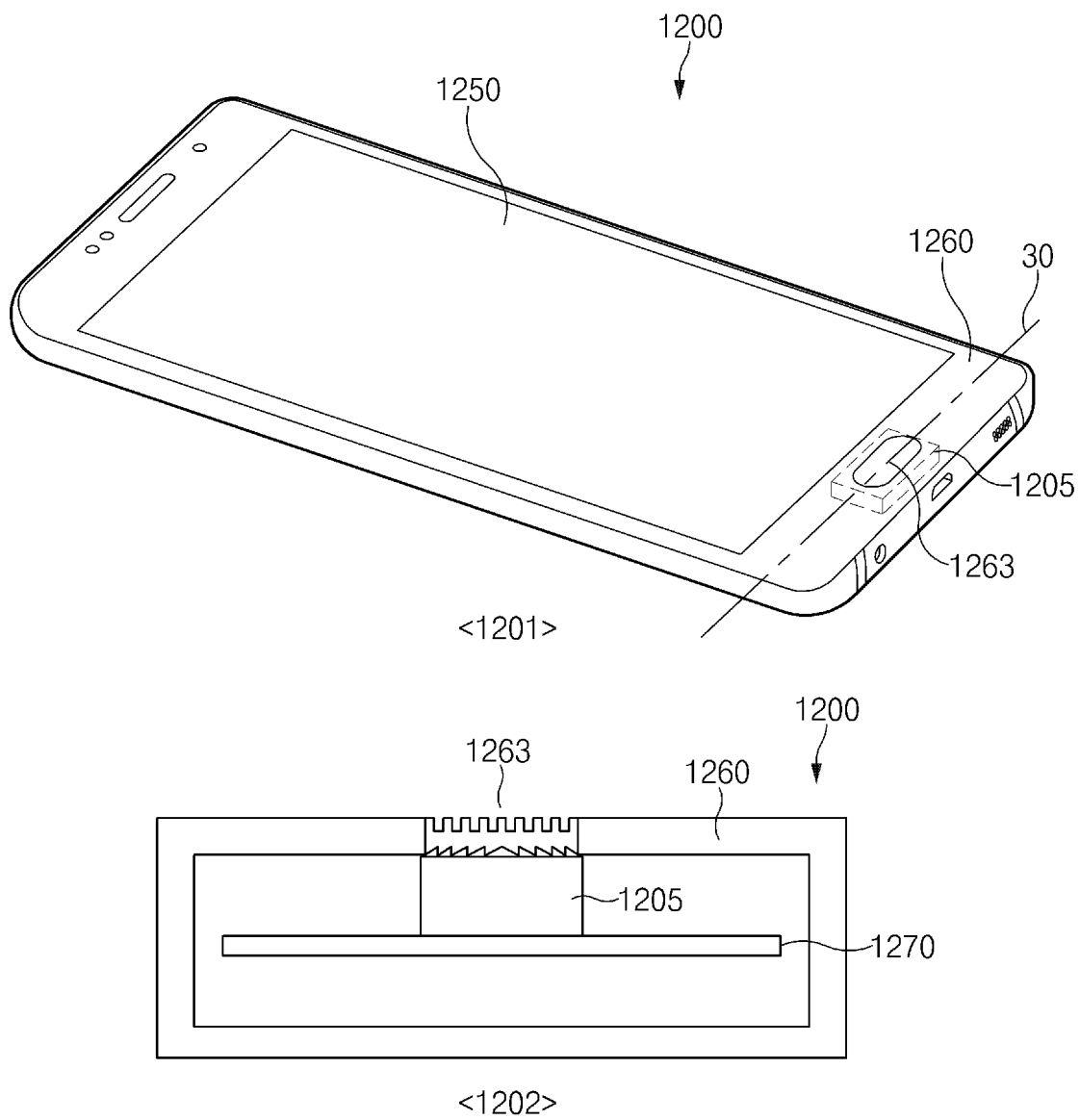
FIG. 12 is a view illustrating a structure of an electronic device, according to one embodiment of the present disclosure.

FIG. 12 is a view illustrating a structure of an electronic device, according to one embodiment of the present disclosure.

The image 1201 illustrates a perspective view of an electronic device 1200 (e.g., the electronic device 701 or the electronic device 801), and an image 1202 illustrates a cross-sectional view taken along a line 30 across the electronic device 1200.

Referring to the image 1201 of FIG. 12, the electronic device 1200 may include a biometric sensor 1205, a display 1250, and a housing 1260. According to an embodiment, the biometric sensor 1205 may be disposed inside the housing 1260 and may be disposed in a region not overlapping with the display 1250. For example, in a front view of the electronic device 1200, the biometric sensor 1205 may be disposed in a region overlapping with a home button 1263 included in the housing 1260.

Referring to the image 1202 of FIG. 12, the biometric sensor 1205 may be disposed under the home button 1263 in the housing 1260. According to an embodiment, at least a partial region of the home button 1263 may be made of a material with high optical transmittance (e.g. glass, transparent polymer, etc.). According to an embodiment, the home button 1263 may include an optical layer in at least a partial region. For example, in a front view of the electronic device 1200, the home button 1263 may include the optical layer in the region corresponding to the biometric sensor 1205. The optical layer included in the home button 1263 may correspond to the optical layers 130, 230, 330, 430, 530, and 630 according to various embodiments illustrated in FIGS. 1 to 6.

According to an embodiment, the electronic device 1200 may include a PCB 1270 (e.g., a flexible printed circuit board (FPCB)) in the housing 1260. The PCB 1270 may be electrically connected with the biometric sensor 1205 and may transmit the electrical signal generated by the biometric sensor 1205 to the sensor IC or the processor included in the electronic device 1200.

According to various embodiments of the present disclosure, the light receiving efficiency of the biometric sensor may increase, and noise included in the biometric signal may decrease.

The term "module" used herein may represent, for example, a unit including one or more combinations of hardware, software and firmware. The term "module" may be interchangeably used with the terms "unit," "logic," "logical block," "component," and "circuit." The "module" may be a minimum unit of an integrated component or may be a part thereof. The "module" may be a minimum unit for performing one or more functions or a part thereof. The "module" may be implemented mechanically or electronically. For example, the "module" may include at least one of an application-specific IC (ASIC) chip, a field-programmable gate array (FPGA), and a programmable-logic device for performing some operations, which are known or will be developed.

According to various embodiments, at least a part of an apparatus (e.g., modules or functions thereof) or a method (e.g., operations) may be, for example, implemented by instructions stored in a computer-readable storage media in the form of a program module. The instruction, when executed by a processor, may cause the one or more processors to perform a function corresponding to the instruction. The computer-readable storage media, for example, may be a memory.

A computer-readable recording medium may include a hard disk, a magnetic media, a floppy disk, a magnetic media (e.g., a magnetic tape), an optical media (e.g., a compact disc read only memory (CD-ROM) and a digital versatile disc (DVD), a magneto-optical media (e.g., a floptical disk), and hardware devices (e.g., a read only memory (ROM), a random access memory (RAM), or a flash memory). Also, a program instruction may include not only a mechanical code such as things generated by a compiler but also a high-level language code executable on a computer using an interpreter. The above-mentioned hardware device may be configured to operate as one or more software modules to perform operations according to various embodiments of the present disclosure, and vice versa.

A module or a program module according to various embodiments of the present disclosure may include at least one of the above-mentioned elements, or some elements may be omitted or other additional elements may be added. Operations performed by the module, the program module or other elements according to various embodiments of the present disclosure may be performed in a sequential, parallel, iterative or heuristic way. Furthermore, some operations may be performed in another order or may be omitted, or other operations may be added.

While the present disclosure has been shown and described with reference to various embodiments thereof, it will be understood by those skilled in the art that various changes in form and details may be made therein without departing from the spirit and scope of the present disclosure as defined by the appended claims and their equivalents.

No claim element herein is to be construed under the provisions of 35 U.S.C. 112, sixth paragraph, unless the element is expressly recited using the phrase "means for." In addition, an artisan understands and appreciates that a "processor" or "microprocessor" may be hardware in the claimed disclosure. Under the broadest reasonable interpretation, the appended claims are statutory subject matter in compliance with 35 U.S.C. § 101.

What is claimed is:

1. A sensor for sensing biometric information, comprising:
   a light emitting unit configured to emit a first light ray;
   a light receiving unit configured to receive a second light ray, wherein the second light ray includes a portion of the first light ray reflected by a body of a user; and
   an optical layer placed over the light emitting unit and the light receiving unit having a first surface facing the light emitting unit and the light receiving unit and a second surface opposite the first surface, wherein the optical layer includes:
an asymmetrical protrusion structure formed on the first surface or the second surface; and
a symmetrical protrusion structure formed on the first surface or the second surface opposite the asymmetrical protrusion structure and including a first plurality of symmetrical protrusion units, the first plurality of symmetrical protrusion units having one or more first heights so as to reduce an amount of light reflected at the first surface or the second surface on which the symmetrical protrusion structure is disposed,
wherein the asymmetrical protrusion structure includes:
a first asymmetrical protrusion structure formed in a first region corresponding to the light emitting unit and including a plurality of asymmetrical protrusion units, the plurality of asymmetrical protrusion units having one or more second heights so as to refract the first light ray further away from the light receiving unit than a direction of the first light ray emitted from the light emitting unit when the first asymmetrical protrusion structure is absent,
wherein the one or more first heights are smaller than the one or more second heights, wherein the one or more first heights are smaller than a first wavelength of the first light ray or a second wavelength of the second light ray, and
wherein the one or more second heights are greater than the first wavelength of the first light ray or the second wavelength of the second light ray.

2. The sensor of claim 1, wherein the asymmetrical protrusion structure further includes:
a second asymmetrical protrusion structure formed in a second region corresponding to the light receiving unit.

3. The sensor of claim 2, wherein the second asymmetrical protrusion structure is configured to refract the second light ray towards an active region of the light receiving unit.

4. The sensor of claim 1, wherein the symmetrical protrusion structure is configured to increase a transmittance of the first light ray and/or the second light ray through the optical layer.

5. The sensor of claim 4, wherein at least some of the plurality of asymmetrical protrusion units include a second plurality of symmetrical protrusion units.

6. The sensor of claim 4, wherein the first plurality of symmetrical protrusion units are spaced apart from each other by one or more specified distances.

7. The sensor of claim 4, further comprising:
a base configured to mount the light emitting unit and the light receiving unit,
wherein the base includes a partition wall interposed between the light emitting unit and the light receiving unit.

8. The sensor of claim 7, wherein:
the light receiving unit includes a first light receiving unit and a second light receiving unit,
the light emitting unit includes a first light emitting unit corresponding to the first light receiving unit and a second light emitting unit corresponding to the second light receiving unit,
the first light receiving unit and the second light receiving unit are disposed in a center region of the base,
the first light emitting unit is disposed at one side of the center region, and
wherein the second light emitting unit is disposed at another side of the center region, the another side being opposite the one side.

9. The sensor of claim 4, further comprising:
at least one of a first waveguide formed between the light emitting unit and the optical layer to guide the first light ray and a second waveguide formed between the light receiving unit and the optical layer to guide the second light ray.

10. The sensor of claim 4, wherein at least a partial region of the optical layer is curved at a specified curvature.

11. An electronic device comprising:
a light emitting unit configured to emit a first light ray;
a light receiving unit configured to receive a second light ray, wherein the second light ray includes a portion of the first light ray reflected by a body of a user;
a processor configured to determine biometric information of the user based on the second light ray; and
a housing including an optical layer, wherein the optical layer has a first surface facing the light emitting unit and the light receiving unit, a second surface opposite the first surface, and the optical layer includes:
an asymmetrical protrusion structure formed on the first surface or the second surface, and
a symmetrical protrusion structure formed on the first surface or the second surface opposite the asymmetrical protrusion structure and including a first plurality of symmetrical protrusion units, the first plurality of symmetrical protrusion units having one or more first heights so as to reduce an amount of light reflected at the first surface or the second surface on which the symmetrical protrusion structure is disposed,
wherein the asymmetrical protrusion structure includes:
a first asymmetrical protrusion structure formed in a first region corresponding to the light emitting unit and including a plurality of asymmetrical protrusion units, the plurality of asymmetrical protrusion units having one or more second heights so as to refract the first light ray further away from the light receiving unit than a direction of the first light ray emitted from the light emitting unit when the first asymmetrical protrusion structure is absent,
wherein the one or more first heights are smaller than the one or more second heights,
wherein the one or more first heights are smaller than a first wavelength of the first light ray or a second wavelength of the second light ray, and
wherein the one or more second heights are greater than the first wavelength of the first light ray or the second wavelength of the second light ray.

12. The electronic device of claim 11, further comprising:
a touch screen,
wherein the optical layer is in a region not overlapping with the touch screen.

13. The electronic device of claim 12, wherein the processor is configured to:
determine heartbeat information of the user based on the second light ray.

14. The electronic device of claim 12, wherein at least some of the plurality of asymmetrical protrusion units include a second plurality of symmetrical protrusion units.

15. The electronic device of claim 12, wherein the asymmetrical protrusion structure further includes:
a second asymmetrical protrusion structure formed in a second region corresponding to the light receiving unit.

16. The electronic device of claim 12, further comprising:
a touch screen, wherein the optical layer is in a region overlapping with the touch screen.

17. An electronic device comprising:
a light emitting unit configured to emit a first light ray;
a light receiving unit configured to receive a second light ray, wherein the second light ray includes a portion of the first light ray reflected by a body of a user;
a housing including an optical layer, wherein the optical layer includes at least one protrusion structure formed on at least one surface of the optical layer; and
a processor configured to determine biometric information of the user based on the second light ray,
wherein the protrusion structure includes:
   a symmetrical protrusion structure including a plurality of symmetrical protrusion units,
   an asymmetrical protrusion structure in a first region corresponding to the light emitting unit and including a plurality of asymmetrical protrusion units, the plurality of asymmetrical protrusion units being configured to refract the first light ray further away from the light receiving unit than a direction of the first light ray emitted from the light emitting unit when the asymmetrical protrusion structure is absent, and
   wherein the plurality of asymmetrical protrusion units have at least one inclined surface, and at least a portion of the symmetrical protrusion structure is disposed on the at least one inclined surface,
wherein the plurality of symmetrical protrusion units have one or more first heights each smaller than a first wavelength of the first light ray or a second wavelength of the second light ray so as to reduce an amount of light reflected at the at least one surface of the optical layer,
wherein the plurality of asymmetrical protrusion units have one or more second heights each greater than the first wavelength of the first light ray or the second wavelength of the second light ray, and
wherein the one or more first heights are smaller than the one or more second heights.

18. The electronic device of claim 17, wherein each symmetrical protrusion unit in the plurality of symmetrical protrusion units has a height substantially equal to ¼ of a wavelength of the first light ray.

* * * * *

UNITED STATES PATENT AND TRADEMARK OFFICE
CERTIFICATE OF CORRECTION

PATENT NO. : 10,776,645 B2
APPLICATION NO. : 15/626367
DATED : September 15, 2020
INVENTOR(S) : Hyun Jae Baek et al.

Page 1 of 1

It is certified that error appears in the above-identified patent and that said Letters Patent is hereby corrected as shown below:

On the Title Page

Item (73), should read as follows:
Assignees: Samsung Electronics Co., Ltd.,
       Suwon-si, Gyeonggi-do (KR);
       Korea Advanced Institute of Science and Technology,
       Yuseong-Gu, Daejeon (KR)

Signed and Sealed this
Thirteenth Day of October, 2020

Andrei Iancu
*Director of the United States Patent and Trademark Office*